(12) United States Patent
Tripp et al.

(10) Patent No.: US 7,371,392 B2
(45) Date of Patent: May 13, 2008

(54) CD40 LIGAND ADJUVANT FOR RESPIRATORY SYNCYTIAL VIRUS

(75) Inventors: Ralph A. Tripp, Decatur, GA (US); Larry J. Anderson, Atlanta, GA (US); Michael P. Brown, St. Georges (AU)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 5 days.

(21) Appl. No.: 10/182,093

(22) PCT Filed: Feb. 2, 2001

(86) PCT No.: PCT/US01/03584

§ 371 (c)(1),
(2), (4) Date: Jul. 25, 2002

(87) PCT Pub. No.: WO01/56602

PCT Pub. Date: Aug. 9, 2001

(65) Prior Publication Data

US 2003/0021808 A1    Jan. 30, 2003

Related U.S. Application Data

(60) Provisional application No. 60/179,905, filed on Feb. 2, 2000.

(51) Int. Cl.
*A61K 39/165* (2006.01)
(52) U.S. Cl. ............................ 424/211.1; 424/184.1; 424/278.1
(58) Field of Classification Search ............ 424/184.1, 424/211.1, 278.1; 530/350
See application file for complete search history.

(56) References Cited

U.S. PATENT DOCUMENTS

| 5,811,524 A | 9/1998 | Brams et al. | |
|---|---|---|---|
| 5,843,913 A | 12/1998 | Li et al. | |
| 5,880,104 A * | 3/1999 | Li et al. | 514/44 |
| 5,939,068 A | 8/1999 | Brams et al. | |

FOREIGN PATENT DOCUMENTS

| WO | WO96/26735 | | 9/1996 |
|---|---|---|---|
| WO | WO 96/26736 | * | 9/1996 |
| WO | WO 98/02180 | | 1/1998 |
| WO | WO 98/02457 | | 1/1998 |
| WO | WO 99/43839 | | 9/1999 |

OTHER PUBLICATIONS

Tripp et al. J of Virology 1998 vol. 72, pp. 8971-8975.*
Gurunathan et al. J. of Immunology 1998 vol. 161, pp. 4563-4571.*
Murphy et al Virus Research 1994 vol. 32, pp. 13-36.*
Ihata et al. "Immunomodulatory effect of a plasmid expressing CD40 ligand on DNA vaccination against human immunodeficiency virus type-1," *Immunology* 98: 436-442 (1999).
Maue, Alexander et al. "CD80 and CD86, but not CD154, argument DNA vaccine-induced protection in experimental bovine tuberculosis" *Vaccine* 23:769-779 (2004).
Miyahira, Yasushi et al. "Cutting Edge: A potent adjuvant effect of ligand to receptor activator of NF-KB Gene for Inducing Antigen-Specific CD8+ T Cell Response by DNA and Viral Vector Vaccination" *J Immunol.* 171:6344-6348 (2003).
Allen et al., "CD40 Ligand Gene Defects Responsible for X-Linked Hyper-IgM Syndrome" *Science* 259:990-993, Feb. 12, 1993.
Anderson et al., "Cytokine Response to Respiratory Syncytial Virus Stimulation of Human Peripheral Blood Mononuclear Cells" *J. Infect. Dis.* 170:1201-1208, Nov. 1994.
Armitage et al., "Molecular and biological characterization of a murine ligand for CD40" *Nature* 357:80-82, May 7, 1992.
Armitage et al., "CD4DL: a multi-functional ligand" *Seminars in Immunol.* 5:401-412, 1993.
Aruffo et al., "The CD40 Ligand, gp39 Is Defective in Activated T Cells from Patients with X-Linked Hyper-IgM Syndrome" *Cell* 72:291-300, Jan. 29, 1993.
Balasa et al., "CD40 Ligand-CD40 Interactions Are Necessary for the Initiation of Insulitis and Diabetes in Nonobese Diabetic Mice" *J. Immunol.* 159(9):4620-4627, 1997.
Banchereau et al., "The CD40 Antigen and its Ligand" *Annu. Rev. Immunol.* 12:881-922, 1994.
Barrett et al., "CD40 Signaling Activates CD11a/CD18 (LFA-1)-Mediated Adhesion in B Cells" *J Immunol.* 146(6):1722-1729, Mar. 15, 1991.
Bennett et al., "Help for a cytotoxic-T-cell responses is mediated by CD40 signalling" *Nature* 393(4):478-480, Jun. 4, 1998.
Borrow et al., "CD40L-deficient Mice Show Deficits in Antiviral Immunity and Have an Impaired Memory CD8 CTL Response" *J. Exp. Med.* 183(5):2129-2142, May 1996.
Briones et al., "In Vivo Antitumor Effect of CD40L-transduced Tumor Cells as a Vaccine for B-Cell Lymphoma" *Cancer Res* 62:3195-3199, Jun. 1, 2002.
Brown et al., "Thymic lymphoproliferative disease after successful correction of CD40 ligand deficiency by gene transfer in mice" *Nat. Med.* 4(11):1253-1260, Nov. 1998.

(Continued)

*Primary Examiner*—Bruce R. Campbell
*Assistant Examiner*—Myron G. Hill
(74) *Attorney, Agent, or Firm*—Klarquist Sparkman, LLP

(57) ABSTRACT

The present invention provides methods and adjuvants for enhancing an immune response to RSV in a host, wherein the methods and adjuvants comprise a source of a CD40 binding protein. Preferably, the CD40 binding protein is CD40L and the source is a vector comprising a promoter operatively linked to a CD40L coding region. The enhanced immune response produced by the adjuvants and methods of the current invention includes both increased expression of Th1 cytokines and increased production of antibody.

10 Claims, 6 Drawing Sheets

OTHER PUBLICATIONS

Caims et al., "Soluble CD23 is released by B lymphocytes cycling in response to interleukin 4 and anti-Bp50 (CDw40)" *Eur. J. Immunol.* 18:349-353, 1988.

Cantwell et al., "T cell activation following infection of primary follicle center lymphoma B cells with adenovirus encoding CD154" *Leukemia* 15:1451-1457, Sep. 2001.

Castigli et al., "CD40-deficient mice generated by recombination-activating gene-2-deficient blaslocyst complementation" *Proc. Natl Acad. Sci. USA* 91:12135-12139, Dec. 1994.

Chaudhary et al., "A recombinant immunotoxin consisting of two antibody variable domains fused to *Pseudomonas* exotoxin" *Nature* 339(6223):394-397, Jun. 1, 1989.

Chin et al., "Field Evaluation of a Respiratory Syncytial Virus Vaccine and a Trivalent Parainfluenza Virus Vaccine in a Pediatric Population" *Am. J. Epidemiol.* 89(4):449-463, 1969.

Clupitu et al., "Immunization with a Lymphocytic Choriomeningitis Virus Peptides Mixed with Heat Shock Protein 70 Results in Protective Antiviral Immunity and Specific Cytotoxic T Lymphocytes" *J. Exp. Med.* 187(5):685-691, Mar. 2, 1998.

Clark et al., "Activation of human B cells mediated through two distinct cell surface differentiation antigens, Bp35 and Bp50" *Proc. Natl. Acad. Sci. USA* 8:4494-4498, Jun. 1986.

Clark et al., "Association Between IL-6 and CD40 Signaling: IL-6 Induces Phosphorylation of CD40 Receptors" *J. Immunol.* 145(5):1400-1406, Sep. 1, 1990.

Collins et al., "Respiratory Syncytial Virus" in Fields B, Knipe D, Howley P., eds., *Fields Virlogy* 3rd ed, Philadelphia: Lippencott-Raven Publishers, Chapter 44 pp. 1313-1351, 1996.

Connors et al., "Enhanced Pulmonary Histopathology Induced by Respiratory Syncytial Virus (RSV) Challenge of Formalin-Inactivated RSV-Immunized BALB/c Mice Is Abrogated by Depletion of Interleukin-4 (IL-4) and IL-10" *J. Virol.* 68(8):5321-5325, Aug. 1994.

Connors et al., "Respiratory Syncytial Virus (RSV) F, G, M2 (22K), and N Proteins Each Induce Resistance to RSV Challenge, but Resistance Induced by M2 and N Proteins Is Relatively Short-Lived" *J. Virol.* 65(3):1634-1637, Mar. 1991.

Cosyns et al., "Requirement of CD40-CD40 Ligand Interaction for Elimination of *Cryptosporidium parvum* from Mice" *Infec. Immun.* 66(2):603-607, Feb. 1998.

Couderc et al., "Enhancement of antitumor immunity by expression of CD70 (CD27 ligand) or CD154 (CD40 ligand) costimulatory molecules in tumor cells" *Cancer Gene Ther.* 5(3):163-175, 1998.

Crowe, "Current approaches to the development of vaccines against disease caused by respiratory syncytial virus (RSV) and parainfluenza virus (PIV)—A meeting report of the WHO Programme foe Vaccine Development" *Vaccine* 13(4):415-421, 1995.

DeKruyff et al., "Antigen-Driven but Not Lipopolysaccharide-Driven Il-12 Production in Macrophages Requires Triggering of CD40" *J. Immunol.* 158:359-366, 1997.

Dilloo et al., "CD 40 Ligand Induces an Antileukemia Immune Response In Vivo" *Blood* 90(5):1927-1933, Sep. 1, 1997.

Doherty, "Vaccines and cytokine-mediated pathology in RSV infection" *Trends Microbiol.* 2(5):148-150, May 1994.

Dolti et al., "Adenovector-induced expression of human-CD40-ligand (hCD40L) by multiple myeloma cells: A model for immunotherapy" *Exp. Hematol.* 29:952-961, Aug. 2001.

Dudas and Karron, "Respiratory Syncytial Virus Vaccines" *Clin. Microbiol. Rev.* 11(3):430-439, Jul. 1998.

Dullforce et al., "Enhancement of T cell-independent immune response in vivo by CD40 antibodies" *Nat. Med.* 4(1):88-91, Jan. 1998.

Durie et al., "The role of CD40 in the regulation of humoral and cell-mediated immunity" *Immunol. Today* 15(9):406-410, 1994.

Falsey and Walsh, "Safety and immunogenicity of respiratory syncytial virus subunit vaccine (PFP-2) in ambulatory adults over age 60" *Vaccine* 14(13):1214-1218, Sep. 1996.

Fixler, "Respiratory Syncytial Virus Infection in Children with Cogenital Heart Disease: A Review" *Pediatr.Cardiol.* 17:163-168, 1996.

Gascan et al., "Anti-CD40 Monoclonal Antibodies or CD4 T Cell Clones and IL-4 Induce IGG4 and IGE Switching in Purified Human B Cells via Different Signaling Pathways" *J. Immunol.* 147(1):8-13, Jul. 1, 1991.

Gordon et al., "Resting B Lymphocytes Can Be Triggered Directly Through The CDw40 (Bp50) Antigen. A Comparison with IL-4-Mediated Signaling" *J. Immunol.* 140(5):1425-1430, Mar. 1, 1988.

Graham et al., "Priming Immunization Determines T Helper Cytokine mRNA Expression Patterns in Lungs of Mice Challenged with Respiratory Syncytial Virus" *J. Immunol.* 151(4):2032-2040, Aug. 15, 1993.

Grewal et al., "Impairment of antigen-specific T-cell priming in mice lacking CD40 ligand" *Nature* 378:617-620, Dec. 7, 1995.

Grewal and Flavell, "The CD40 Ligand. At the Center of the Immune Universe?" *Immunol. Res.* 16:59-70, Feb. 1997.

Groothuis et al., "Safety and Immunogenicity of a Purified F Protein Respiratory Syncytial Virus (PFP-2) Vaccine in Seropositive Children with Bronchopulmonary Dysplasia" *J. Infect. Dis.* 177:467-469, Feb. 1998.

Groothuis et al., "Use of Intravenous Gamma Globulin To Passively Immunize High-Risk Children against Respiratory Syncytial Virus: Safety and Pharmacokinetics" *Antimicrobial Agents & Chemotherapy* 35(7):1469-1473, Jul. 1991.

Gurunathan et al., "CD40 Ligand/Trimer DNA Enhances Both Humoral and Cellular Immune Responses and Induces Protective Immunity to Infectious and Tumor Challenge" *J. Immunol.* 161:4563-4571, 1998.

Hall et al., "Immunity to and Frequency of Reinfection with Respiratory Syncytial Virus" *J. Infect. Dis.* 163:693-698, Apr. 1991.

Han et al., "Respiratory Syncytial Virus Pneumonia among the Elderly: An Assessment of Disease Burden" *J. Infect. Diseases* 179:25-30, 1999.

Hancock et al., "Formulation of the purified fusion protein of respiratory syncytial virus with the saponin QS-21 induces protective immune responses in Balb/c mice that are similar to those generated by experimental infection" *Vaccine* 13(4):391-400, 1995.

Hemming et al., "Hyperimmune Globulins in Prevention and Treatment of Respiratory Syncytial Virus Infections" *Clinical Microbiol. Rev.* 8(1):22-33, Jan. 1995.

Henderson et al., "Respiratory-Syncytial-Virus Infections, Reinfections and Immunity: A Prospective, Longitudinal Study in Young Children" *N. Engl. J. Med.* 300(10):530-534, Mar. 8, 1979.

Hill and Chapel, "X-Linked immunodeficiency—The fruits of cooperation" *Nature* 361:494, Feb. 11, 1993.

Hussell et al., "Th1 and Th2 cytokine induction in pulmonary T cells during infection with respiratory syncytial virus" *J. Gen. Virol.* 77:2447-2455, Oct. 1996.

Jabara et al., "CD40 and IgE: Synergism between Anti-CD40 Monoclonal Antibody and Interleukin 4 in the Induction of IgE Synthesis by Highly Purified Human B Cells" *J. Exp. Med.* 172:1861-1864, Dec. 1990.

Jiang et al., "Local High-Capacity Adenovirus-Mediated mCTLA4lg and mCD40lg Expression Prolongs Recombinant Gene Expression in Skeletal Muscle" *Mol. Ther.* 3(6):892-900, Jun. 2001.

Karron et al., "Evaluation of Two Live, Cold-Passaged, Temperature-Sensitive Respiratory Syncytial Virus Vaccines in Chimpanzees and in Human Adults, Infants, and Children" *J. Infect. Diseases* 176:1428-1436, Dec. 1997.

Kawabe et al., "The Immune Responses in CD40-Deficient Mice: Impaired Immunoglobulin Class Switching and Germinal Center Formation" *Immunity* 1:167-178, Jun. 1994.

Kennedy et al., "CD40/CD40 ligand interactions are required for T cell-dependent production of interleukin-12 mouse macrophages" *Eur. J. Immunol.* 26:370-378, 1996.

Kikuchi et al., "Tumor Regression Induced by Intratumor Administration of Adenovirus Vector Expressing CD40 Ligand and Naïve Dendritic Cells" *Cancer Res.* 60(22):6391-6395, Nov. 15, 2000.

Kikuchi et al., "Dendritic cells modified to express CD40 ligand elicit therapeutic immunity against preexisting murine tumors" *Blood* 96(1):91-9, Jul. 1, 2000.

Kikuchi et al., "Dendritic cells genetically modified to express CD40 ligand and pulsed with antigen can initiate antigen-specific humoral immunity independent of CD4 T cells" *Nat. Med.* 6(10):1154-1159, Oct. 2000.

Klaus et al., "CD40 and its ligand in the regulation of humoral immunity" *Seminars in immunol.* 6:279-286, Oct. 1994.

Kuwashima et al., "CD 40 Ligand immunotherapy in Cancer: An Efficient Approach" *Leuk. Lymphoma* 42:1367-1377, 2001.

Laman et al., "Functions of CD40 and its Ligand, gp39 (CD40L)" *Crit. Rev. Immunol.* 16:59-108, 1996.

Larrick et al., "Polymerase Chain Reaction Using Mixed Primers: Cloning of Human Monoclonal Antibody Variable Region Genes From Single Hybridoma Cells" *Biotechnology* 7:934-938, Sep. 1989.

Lei et al., "Disruption of Antigen-induced inflammatory Responses in CD40 Ligand Knockout Mice" *J. Clin. Invest.* 101(6):1342-1353, Mar. 15, 1998.

Leimig et al., "High-Efficiency Transduction of Freshly Isolated Human Tumor Cells Using Adenoviral Interleukin-2 Vectors" *Hum. Gene Ther,* 7:1233-1239, Jun. 20, 1996.

Leong et al., "Selective Induction of Immune Responses by Cytokines Coexpressed in Recombinant Fowlpox Virus" *J. Virol.* 68(12):8125-8130, Dec. 1994.

Liu et al., "Adenovirus-mediated CD40 ligand gene-engineered dendritic cells elicit enhanced CD8+ cytotoxic T-cell activation and antitumor immunity", *Cancer Gene Ther.* 9(2):202-208, Feb. 2002.

MacMicking et al., "Nitric Oxide and Microphage Function" *Annu. Rev. Immunol.* 15:323-350, 1997.

Murphy et al., "An update on approaches to the development of respiratory syncytial virus (RSV) and parainfluenza virus type 3 (PIV3) vaccines" *Virus Res.* 32:13-36, 1994.

Murphy et al., "Current approaches to the development of vaccines effective against parainfluenza and respiratory syncytial viruses" *Virus Res.* 11:1-15, Aug. 1988.

Neuzil et al., "Adjuvants influence the quantitative and qualitative immune response in BALB/c mice immunized with respiratory syncytial virus FG subunit vaccine" *Vaccine* 15(5):525-532,1997.

Noelle et al., "CD40 and its ligand in cell-mediated immunity" *Agents & Actions—Supplements* 49:17-22, 1998.

Ostrowski et al., "The Role of CD4+ T Cell Help and CD40 Ligand in the In Vitro Expansion of HIV-1-Specific Memory Cytotoxic CD8+ T Cell Reponses" *J. Immunol.* 165(11):6133-6141, Dec. 2000.

Oxenius et al., "CD40-CD40 ligand interactions are critical in T-B cooperation but not for other anti-viral CD4+ T cell functions" *J. Exp. Med.* 183:2209, 1996.

Paulie et al., "The Human B Lymphocyte and Carcinoma Antigen, CDw40, Is A Phosphoprotein Involved in Growth Signal Transduction" *J. Immunol.* 142(2):590-595, Jan. 15, 1989.

Perkus et al., "Poxvirus-based vaccine candidates for cancer, AIDS, and other infectious diseases" *J. Leukocyte Biol.* 58:1-13, Jul. 1995.

Piedra et al., "Purified fusion protein vaccine protects against lower respiratory tract illness during respiratory syncytial virus season in children with cystic fibrosis" *Pediatr. Infect. Disease J.* 15(1):23-31, 1996.

Pope et al., "Resistance to Murine Hepatilis Virus Strain 3 Is Dependent on Production of Nitric Oxide" *J. Virol.* 72(9):7084-7090, Sep. 1998.

Ramsay et al., "Enhancement of Muscosal IgA Responses by Interleukins 5 and 6 Encoded in Recombinant Vaccine Vectors" *Reprod. Fertil. Dev.* 6:389-392, 1994.

Ramshaw et al., "Cytokines and immunity to viral infections" *Immunol. Rev.* 159:119-135, 1997.

Ramshaw et al., "Recovery of immunodeficient mice from a vaccina virus/IL-2 recombinant infection" *Nature* 329:545-546, Oct. 8, 1987.

Reichmann et al., "Reshaping human antibodies for therapy" *Nature* 332:323-327, Mar. 24, 1988.

Ridge et al., "A conditioned dendritic cell can be a temporal bridge between a CD4+ T-helper and a T-killer" *Nature* 393:474-478, Jun. 4, 1998.

Roberts et al., "Generation of an antibody with enhanced affinity and specificity for its antigen by protein engineering" *Nature* 328(6132):731-734, Aug. 20, 1987.

Ruby et al., "CD40 ligand has potent antiviral activity" *Nat Med.* 1(5):437-441, May 1995.

Schmitz et al., "Adenovirus-Mediated CD40 Ligand Gene Therapy in a Rat Model of Orthotopic Hepatocellular Carcinoma" *Hepatology* 34(1):72-81, Jul. 2001.

Siegrist et al., "Protective Efficacy against Respiratory Syncytial Virus following Murine Neonatal Immunization with BBG2Na Vaccine: Influence of Adjuvants and Maternal Antibodies" *J. Infect. Dis.* 179:1326-1333, Jun. 1999.

Sin et al., "Modulation of Cellular Responses by Plasmid CD40L: CD40L Plasmid Vectors Enhance Antigen-Specific Helper T Cell Type 1 CD4+ T Cell-Mediated Protective Immunity Against Herpes Simplex Virus Type 2 in Vivo" *Hum. Gene Ther.* 12:1091-102, Jun. 10, 2001.

Skiadopoulos et al., "Attenuation of the Recombinant Human Parainfluenza Virus Type 3 cp45 Candidate Vaccine Virus Is Augmented by Importation of the Respiratory Syncytial Virus cpts530 L Polymerase Mutation" *Virology* 260:125-135, 1999.

Soong et al., "Disruption of CD40-CD40 Ligand Interactions Results in an Enhanced Susceptibility to *Leishmania amazonensis* Infection" *Immunity* 4:263-273, Mar. 1996.

Spriggs et al., "Recombinant Human CD40 Ligand Stimulates B Cell Proliferation and Immunoglobulin E Secretion" *J. Exp. Med.* 176:1543-1550, Dec. 1992.

Srikiatkhachom et al., "Virus-Specific Memory and Effector T Lymphocytes Exhibit Different Cytokine Responses to Antigens during Experimental Murine Respiratory Syncytial Virus Infection" *J. Virol.* 71(1):678-685, Jan. 1997.

Stamenkovic et al., "A B-lymphocyte activation molecule related to the nerve growth factor receptor and induced by cytokines in carcinomas" *Embo J.* 8(5):1403-1410, 1989.

Stott et al., "Immune and Histopathological Responses in Animals Vaccinated with Recombinant Vaccinia Viruses That Express Individual Genes of Human Respiratory Syncytial Virus" *J. Virol.* 61(12):3855-3861, Dec. 1987.

Stoul et al., "Impaired T Cell-Mediated Macrophage Activation In CD40 Ligand-Deficient Mice" *J. Immunol.* 156:8-11, 1996.

Sullender, "Antigenic Analysis of Chimeric and Truncated G Proteins of Respiratory Syncytial Virus" *Virology* 209:70-79, May 10, 1995.

Sun et al., "In vivo gene transfer of CD40 ligand into colon cancer cells induces local production of cytokines and chemokines, tumor eradication and protective antitumor immunity" *Gene Ther.* 7:1467-1476, Sep. 2000.

Teng and Collins, "Altered Growth Characteristics of Recombinant Respiratory Syncytial Viruses Which Do Not Produce NS2 Protein" *J. Virol.* 73(1):466-473, 1999.

Tripp et al., "CD40 Ligand (CD154) Enhances the Th1 and Antibody Responses to Respiratory Syncytial Virus in the BALB/c Mouse" *J. Immunol.* 164(11):5913-5921, Jul. 2000.

Tripp and Anderson, "Cytotoxic T-Lymphocyte Precursor Frequencies in BALB/c Mice after Acute Respiratory Syncytial Virus (RSV) Infection of Immunization with a Formalin-Inactivated RSV Vaccine" *J. Virol.* 72(11):8971-8975, Nov. 1998.

Valle et al., "Activation of human B lymphocytes through CD40 and iInterleukin 4" *Eur. J. Immunol.* 19:1463-1467, 1989.

Van Kooten and Banchereau, "Functional Role of CD40 and Its Ligand" *Intl. Arch. Allergy & Immunol.* 113:393-399, 1997.

Van Kooten and Banchereau, "Functions of CD40 on B cells, dendritic cells and other cells" *Curr. Opin. Immunol.* 9:330-337, Jun. 1997.

Verhoeyen et al., "Reshaping Human Antibodies: Grafting an Antilysozyme Activity" *Science* 239(4847):1534-1536, 1988.

Waris et al., "Respiratory Syncytial Virus Infection in BALB/c Mice Previously Immunized with Formalin-Inactivated Virus Induces Enhanced Pulmonary Inflammatory Response with a Predominant Th2-Like Cytokine Patterns" *J Virol.* 70(5):2852-2860, May 1998.

Welliver et al., "Ciinical and Laboratory Diagnosis of Respiratory Syncytial Virus Infection" *Crit. Rev. Clin. Lab. Sci.* 13:213-239, Jan. 1981.

Whitehead et al., "Addition of a Missense Mutation Present in the L Gene of Respiratory Syncytial Virus (RSV) cpts530/1030 to RSV Vaccine Candidate cpts248/404 Increases Its Attenuation and Temperature Sensitivity" *J. Virol.* 73(2):871-877, Feb. 1999.

Wierda et al., "CD40-ligand (CD154) gene therapy for chronic lymphocytic leukemia" *Blood* 96(9):2917-2924, Nov. 2000.

Wolff et al., "Direct Gene Transfer into Mouse Muscle in Vivo" *Science* 247(4949):1465-1468, Mar. 23, 1990.

Xin et al., "Immunization of RANTES Expression Plasmid with a DNA Vaccine Enhances HIV-1-Specific Immunity" *Clinical Immunol.* 92(1):90-96, Jul. 1999.

Yang et al., "Transient Subversion of CD40 Ligand Diminishes Immune Responses to Adenovirus Vectors in Mouse Liver and Lung Tissues" *J. Virol.* 70(9):6370-6377, Sep. 1996.

\* cited by examiner

Anti-RSV Antibody Binding Ratios

| Category | Absorbance Ratio |
|---|---|
| F | ~4.2 |
| CD40L-F | ~7.2 |
| G | ~0.4 |
| CD40L-G | ~2.85 |
| F-G | ~2.6 |
| CD40L-F-G | ~5.0 |

FIG.6

SEQUENCE LISTING

```
<160> NUMBER OF SEQ ID NOS: 1

<210> SEQ ID NO 1
<211> LENGTH: 1250
<212> TYPE: DNA
<213> ORGANISM: Murine

<400> SEQUENCE: 1
ctttcagtca gcatgataga aacatacagc caaccttccc ccagatccgt ggcaactgga      60
cttccagcga gcatgaagat ttttatgtat ttacttactg ttttccttat cacccaaatg     120
attggatctg tgcttttttgc tgtgtatctt catagaagat tggataaggt cgaagaggaa     180
gtaaaccttc atgaagattt tgtattcata aaaaagctaa agagatgcaa caaggagaa      240 ggatctttat ccttgctgaa ctgtgaggag atgagaaggc aatttgaaga ccttgtcaag     300
gatataacgt taaacaaaga agagaaaaaa gaaaacagct ttgaaatgca aagaggtgat     360
gaggatcctc aaattgcagc acacgttgta agcgaagcca acagtaatgc agcatccgtt     420
ctacagtggg ccaagaaagg atattatacc atgaaaagca acttggtaat gcttgaaaat     480
```

-continued

```
gggaaacagc tgacggttaa aagagaagga ctctattatg tctacactca agtcaccttc      540
tgctctaatc gggagccttc gagtcaacgc ccattcatcg tcggcctctg gctgaagccc      600
agcattggat ctgagagaat cttactcaag gcggcaaata cccacagttc ctcccagctt      660
tgcgagcagc agtctgttca cttgggcgga gtgtttgaat tacaagctgg tgcttctgtg      720
tttgtcaacg tgactgaagc aagccaagtg atccacagag ttggcttctc atcttttggc      780
ttactcaaac tctgaacagt gcgctgtcct aggctgcagc agggctgatg ctggcagtct      840
tccctataca gcaagtcagt taggacctgc cctgtgttga actgcctatt tataaccota      900 ggatcctcct catggagaac tatttattat gtaccoccaa ggcacataga gctggaataa      960
gagaattaca gggcaggcaa aaatcccaag ggaccctgct ccctaagaac ttacaatctg     1020
aaacagcaac cccactgatt cagacaacca gaaaagacaa agccataata cacagatgac     1080
agagctctga tgaaacaaca gataactaat gagcacagtt ttgttgtttt atgggtgtgt     1140
cgttcaatgg acagtgtact tgacttacca gggaagatgc agaagggcaa ctgtgagcct     1200
cagctcacaa tctgttatgg ttgacctggg ctccctgcgg ccctagtagg              1250
```

CD40 LIGAND ADJUVANT FOR RESPIRATORY SYNCYTIAL VIRUS

This application is a 371 of PCT/US01/03584, filed Feb. 2, 2001, which claims priority to U.S. provisional application Ser. No. 60/179,905 filed Feb. 2, 2000. The 60/179,905 provisional patent application is herein incorporated by this reference in its entirety.

FIELD OF THE INVENTION

The present invention relates to adjuvants and methods for enhancing an immune response to respiratory syncytial virus.

BACKGROUND

Worldwide, the most important cause of bronchiolitis and serious lower respiratory tract disease in infants and young children is respiratory syncytial virus (RSV) (Collins et al., "Respiratory syncytial virus," IN: Fields B, Knipe, D., Howley P., eds. *Fields Virology.* 3rd ed. 1. Philadelphia: Lippencott-Raven Publishers:1313 (1996); Crowe, J. E., Jr., "Current approaches to the development of vaccines against disease caused by RSV and parainfluenza virus (PIV)," Meeting Report, WHO Programme for Vaccine Development. *Vaccine* 13:415 (1995); and Welliver et al., "Clinical and laboratory diagnosis of respiratory syncytial virus infection," *Critical Reviews in Clinical Laboratory Sciences* 13:213 (1981)). Natural infection with RSV provides limited protection from reinfection and disease as demonstrated by recurrence of severe RSV infections throughout life (Hall et al., "Immunity to and frequency of reinfection with respiratory syncytial virus," *J. Infect. Dis.* 163:693 (1991); and Henderson et al., "Respiratory syncytial virus infections, reinfections and immunity: a prospective. Longitudinal study in young children," *N. Engl. J. Med.* 300:530 (1979)). Moreover, the peak incidences of serious RSV disease are in young infants who have maternally-acquired neutralizing RSV antibodies. Thus, the development of RSV vaccines has long been a priority for infants and young children (Crowe, J. E. Jr., "Current approaches to the development of vaccines against disease caused by respiratory syncytial virus (RSV) and parainfluenza virus (PIV). A meeting report of the who programme for vaccine development," *Vaccine* 13:415 (1995); "New vaccine development: establishing priorities; diseases of importance in the United States," Washington D.C., *Institute of Medicine National Academy Press* (1985); "New vaccine development: establishing priorities, diseases of importance in developing countries," Washington D.C. *National Academy Press II* (1986); Doherty P. C., "Vaccines and cytokine-mediated pathology in RSV infection," *Trends in Microbiology* 2:148 (1994); and Murphy et al., "Current approaches to the development of vaccines effective against parainfluenza and respiratory syncytial viruses," *Virus Research* 11:1 (1988)). More recently, vaccines are being developed for older children at risk for serious complications of infection and for the elderly (Piedra et al., "Purified fusion protein vaccine protects against lower respiratory tract illness during respiratory syncytial virus season in children with cystic fibrosis," *Pediatric Infectious Disease Journal* 15:23 (1996); Han et al., "Respiratory syncytial virus pneumonia among the elderly: an assessment of disease burden," *Journal of Infectious Diseases* 179:25 (1999); and Falsey et al., "Safety and immunogenicity of a respiratory syncytial virus subunit vaccine (PFP-2) in ambulatory adults over age 60," *Vaccine* 14:1214 (1996)).

RSV vaccine development has been focused toward live, temperature sensitive, attenuated vaccines and subunit vaccines based on the F and/or G glycoproteins (Groothuis et al., "Safety and Immunogenicity of a purified F protein respiratory syncytial virus (PFP-2) vaccine in seropositive children with bronchopulmonary dysplasia," *Journal of Infectious Diseases* 177:467 (1998); Neuzil et al., "Adjuvants influence the quantitative and qualitative immune response in BALB/c mice immunized with respiratory syncytial virus FG subunit vaccine," *Vaccine* 15:525 (1997); and Siegrist et al., "Protective efficacy against respiratory syncytial virus following murine neonatal immunization with BBG2NA vaccine: influence of adjuvants and maternal antibodies," *Journal of Infectious Diseases* 179:1326 (1999)). In animal model systems, the F glycoprotein is generally the most effective with the G glycoprotein being the next most effective in inducing neutralizing antibodies and protective immunity. Vaccination with the G glycoprotein, however, generally induces only limited protection (Stott et al., "Immune and histopathological responses in animals vaccinated with recombinant vaccinia viruses that express individual genes of human respiratory syncytial virus," *J. Virol.* 61:3855 (1987); and Connors et al., "Respiratory syncytial virus (RSV) F, G, M2 (22K), and N proteins each induce resistance to RSV challenge, but resistance induced by M2 and N proteins is relatively short-lived," *Journal of Virology* 65:1634 (1991)). In clinical studies, no vaccine has yet proven safe and efficacious, mainly because candidate live virus vaccines have been under or over attenuated or have reverted to wildtype phenotype (Karron et al., "Evaluation of two live, cold-passaged, temperature-sensitive respiratory syncytial virus vaccines in chimpanzees and in human adults, infants, and children," *Journal of Infectious Diseases* 176:1428 (1997)). However, the recent availability of an RSV infectious clone has expanded the options in developing live virus candidate vaccine strains, and renewed hope that a safe and efficacious live virus vaccine can be developed (Teng et al., "Altered growth characteristics of recombinant respiratory syncytial viruses which do not produce NS2 Protein," *Journal of Virology* 73:466 (1999); Skiadopoulos et al., "Attenuation of the recombinant human parainfluenza virus type 3 CP45 candidate vaccine virus is augmented by importation of the respiratory syncytial virus CPTS530 L polymerase mutation," *Virology* 260:125 (1999); and Whitehead et al., "Addition of a missense mutation present in the 1 gene of respiratory syncytial virus (RSV) CPTS530/1030 to RSV vaccine candidate CPTS248/404 increases its attenuation and temperature sensitivity," *Journal of Virology* 73:871 (1999)). Nevertheless, there remains a need for efficacious methods and adjuvants for enhancing the safety and efficacy of RSV vaccines.

Development of subunit vaccines, in particular, has been hindered by concerns about the enhanced lung disease that occurred in young children who received a formalin-inactivated RSV (FI-RSV) vaccine, and then had natural RSV infection (Chin et al., "Field evaluation of a respiratory syncytial virus vaccine and a trivalent parainfluenza virus vaccine in a pediatric population," *Am J Epidemiol* 89:449 (1969)). Although the reasons for this vaccine-augmented disease remain uncertain, evidence in the BALB/c mouse model suggests that a heightened Th2 cytokine response may in part be responsible (Anderson et al., "Cytokine Response to respiratory syncytial virus stimulation of human peripheral blood mononuclear cells," *Journal of Infectious Diseases* 170:1201 (1994); Connors et al., "Enhanced pulmonary histopathology induced by respiratory syncytial virus (RSV) challenge of formalin-inactivated RSV-immunized BALB/c mice is abrogated by depletion of interleukin-4 (IL-4) and IL-10," *Journal of Virology* 68:5321 (1994); and Waris et al., "Respiratory synctial virus infection in BALB/c mice previously immunized with formalin-inactivated virus induces enhanced pulmonary inflammatory response with a predominant TH2-like cytokine pattern," *Journal of Virology* 70:2852 (1996)). In these studies, enhanced lung pathology in FI-RSV vaccinated mice challenged with live RSV was shown to be mediated by Th2-type CD4+ T cells expressing IL-4, IL-5, IL-6, and IL-10. In contrast, mice immunized and challenged with live RSV do not develop extensive lung pathology and respond with a mixed Th1/Th2 immune response (Anderson et al. (1994); Graham et al., "Priming immunization determines T helper cytokine mRNA expression patterns in lungs of mice challenged with respiratory syncytial virus," *Journal of Immunology* 151:2032 (1993); Hussell et al., "Th1 and Th2 cytokine induction in pulmonary T cells during infection with respiratory syncytial virus," *Journal of General Virology* 77:2447 (1996); and Srikiatkhachom et al., "Virus-specific memory and effector T lymphocytes exhibit different cytokine responses to antigens during experimental murine respiratory syncytial virus infection," *Journal of Virology* 71:678 (1997)). Based on this possible role of a heightened Th2 cytokine response in enhancing lung disease upon live RSV infection, there is a need for methods and/or reagents for promoting a Th1 response over a Th2 response to live viral challenge.

Since passive administration of high titered neutralizing RSV antibodies can decrease the risk of serious RSV disease, one of the best indicators of protection from RSV disease is high titers of neutralizing antibodies (Groothuis et al., "Use of intravenous gamma globulin to passively immunize high-risk children against respiratory syncytial virus: safety and pharmacokinetics. The RSVIG study group," *Antimicrobial Agents & Chemotherapy* 35:1469 (1991); and Hemming et al., "Hyperimmune globulins in prevention and treatment of respiratory syncytial virus infections," *Clinical Microbiology Reviews* 8:22 (1995)). Unfortunately, both attenuated live and subunit candidate vaccines induce only modest increases in antibodies (Dudas et al., "Respiratory syncytial virus vaccines," *Clinical Microbiology Reviews* 11:430 (1998); and Murphy et al., "An update on approaches to the development of respiratory syncytial virus (RSV) and parainfluenza virus type 3 (PIV3) vaccines," *Virus Research* 32:13 (1994)). As evidenced by the variety of adjuvants that are being evaluated for their ability to enhance the immune response to subunit vaccines (See e.g., Xin et al., "Immunization of rantes expression plasmid with a DNA vaccine enhances HIV-1-specific Immunity," *Journal of Applied Biomaterials (Orlando)* 92:90 (1999); Ciupitu et al., "Immunization with a lymphocytic choriomeningitis virus peptide mixed with heat shock protein 70 results in protective antiviral immunity and specific cytotoxic T lymphocytes," *Journal of Experimental Medicine* 187:685 (1998); and Hancock et al., "Formulation of the purified fusion protein of respiratory syncytial virus with the saponin QS-21 induces protective immune responses in BALB/c Mice that are similar to those generated by experimental infection," *Vaccine* 13:391 (1995)), there remains a need for an adjuvant that is effective at enhancing immune responses to RSV vaccines, especially subunit vaccines.

One potential immune-enhancing molecule is CD40L which is important to productive interactions between T cells and antigen presenting cells (Armitage et al., "CD401: a multi-functional ligand," *Seminars in Immunology* 5:401 (1993); Grewal et al., "The CD40 Ligand. At the center of the immune universe?" *Immunologic Research* 16:59 (1997); Laman et al., "Functions of CD40 and its ligand, GP39 (Cd401)," *Critical Reviews in Immunology* 16:59 (1996); Ramshaw et al., "Cytokines and immunity to viral infections," *Immunological Reviews* 159:119 (1997); van Kooten et al., "Functional role of CD40 and its ligand," *International Archives of Allergy & Immunology* 113:393 (1997); van Kooten et al., "Functions of CD40 on B cells, dendritic cells and other cells," *Current Opinion in Immunology* 9:330 (1997); Bennett et al., "Help for a cytotoxic-T-cell response is mediated by CD40 signaling," *Nature* 393:478 (1998); and Ridge et al., "A conditioned dendritic cell can be a temporal bridge between a CD4+T-helper and a T-killer," *Nature* 393:474 (1998)). CD40L has been shown to enhance both humoral and cellular immune responses (Grewal et al. (1997); Laman (1996); Gurunathan et al., "CD40 ligand/trimer DNA enhances both humoral and cellular immune responses and induces protective immunity to infectious and tumor challenge," *Journal of Immunology* 161:4563 (1998); and Durie et al., "The role of CD40 in the regulation of humoral and cell-mediated immunity," *Immunology Today* 15:406 (1994); Klaus et al., "CD40 and its ligand in the regulation of humoral immunity," *Seminars in Immunology* 6:279 (1994); and Noelle et al., "CD40 and its ligand in cell-mediated immunity," *Agents & Actions— Supplements* 49:17 (1998)). For example, CD40L expression has been shown to enhance T cell and APC activation and signaling, the importance of which has been revealed by studies of CD40L$^{-/-}$ mice (Borrow et al., "CD40L-deficient mice show deficits in antiviral immunity and have an impaired memory CD8+ CTL response," *Journal of Experimental Medicine* 183:2129 (1996); Castigli et al., "CD40-deficient mice generated by recombination-activating gene-2-deficient blastocyst complementation," *Proceedings of the National Academy of Sciences of the United States of America* 91:12135 (1994); Cosyns et al., "Requirement of CD40-CD40 ligand interaction for elimination of *Cryptosporidium parvum* from mice," *Infection & Immunity* 66:603 (1998); Grewal et al., "Impairment of antigen-specific T-cell priming in mice lacking CD40 ligand," *Nature* 378:617 (1995); Kawabe et al., "The immune responses in CD40-deficient mice: impaired immunoglobulin class switching and germinal center formation," *Immunity* 1:167 (1994); Kennedy et al., "CD40/CD40 ligand interactions are required for T cell-dependent production of interleukin-12 by mouse macrophages," *European Journal of Immunology* 26:370 (1996); Lei et al., "Disruption of antigen-induced inflammatory responses in CD40 ligand knockout mice," *Journal of Clinical Investigation* 101:1342 (1998); Soong et al., "Disruption of CD40-CD40 ligand interactions results in an enhanced susceptibility to *Leishmania amazonensis* infection," *Immunity* 4:263 (1996); and Stout et al., "Impaired T cell-mediated macrophage activation in CD40 ligand-deficient mice," *Journal of Immunology* 156:8 (1996)) and in CD40L$^{-/-}$ humans (Allen et al., "CD40 ligand gene defects responsible for X-linked hyper-IgM syndrome," *Science* 259:990 (1993)). Coincident expression of CD40L has been shown to promote T cell mediated immunity (Ramshaw et al. (1997); Yang et al., "Transient subversion of CD40 ligand function diminishes immune responses to adenovirus vectors in mouse liver and lung tissues," *Journal of Virology* 70:6370 (1996); Ruby et al., "CD40 ligand has potent antiviral activity," *Nature Medicine* 1:437 (1995); Couderc et al., "Enhancement of antitumor immunity by expression of CD70 (CD27 ligand) or CD154 (CD40 ligand) costimulatory molecules in tumor cells,"

Cancer Gene Therapy 5:163 (1998); and Brown et al., "Thymic lymphoproliferative disease after successful correction of CD40 ligand deficiency by gene transfer in mice," Nature Medicine 4:1253 (1998)). Administering anti-CD40 monoclonal antibody to mice together with pneumococcal polysaccharide generated strong, isotype-switched antibody responses (Dullforce et al., "Enhancement of T cell-independent immune responses in vivo by CD40 antibodies," Nature Medicine 4:88 (1998)). Immunization of BALB/c mice with DNA plasmids expressing β-galactosidase and a protein consisting of CD40L linked to a leucine zipper motif increased the Th1-type immune response to β-galactosidase (Gurunathan et al. (1998)). The importance of CD40L expression in the development of Th1 cytokine responses was also demonstrated by antibody inhibition studies in which anti-CD40L antibody decreased Th1-mediated autoimmune diabetes in NOD mice by reducing IL-12 secretion and slightly increasing IL-4 production (Balasa et al., "CD40 ligand-CD40 interactions are necessary for the initiation of insulitis and diabetes in nonobese diabetic mice," Journal of Immunology 159:4620 (1997)).

Several studies that utilized CD40L deficient mice reveal a role for CD40L in both humoral and cellular immune responses to viruses. Constitutive retroviral expression of CD40L restored antigen-specific cytolytic and humoral immune responses in CD40L$^{-/-}$ mice infected intranasally with the HKx31 strain of influenza (Brown et al. (1998)). Infection of mice with recombinant vaccinia virus that expressed CD40L markedly enhanced viral clearance by both an IFNγ-dependent mechanism and a novel CD40L-dependent mechanism (Ruby et al. (1995)). In studies that examined the anti-adenovirus response in CD40L$^{-/-}$ mice, diminished CD4$^+$ T cell priming and reduced IL4, IL-10 and IFNγ cytokine expression occurred in the absence of CD40L (Yang et al. (1996)). A role for CD40L in antiviral B and T cell immune responses was also shown in CD40L$^{-/-}$ mice challenged with lymphocytic choriomeningitis virus (LCMV), (Borrow et al. (1996); Oxenius et al., "CD40-CD40 ligand interactions are critical in T-B cooperation but not for other anti-viral CD4$^+$ T cell functions," Journal of Experimental Medicine 183:2209 (1996)). CD40L$^{-/-}$ mice infected with LCMV were capable of generating primary CTL responses, but had defective memory CTL responses. Furthermore, primary anti-LCMV IgG1 antibody responses were severely impaired in the absence of CD40L. Although an involvement of CD40L in immune responses has been established, it has not been established or suggested that CD40L, or vectors capable of expressing CD40L, are effective in enhancing an immune response, especially a Th1 cytokine immune response, to RSV.

Li et al. ("Nucleic Acid Respiratory Syncytial Virus Vaccines," U.S. Pat. Nos. 5,880,104 (1999) and 5,843,913 (1998)) describe vaccines for RSV that utilize the RSV F protein expressed from the cytomegalovirus promoter.

Brams et al. ("Neutralizing High Affinity Human Monoclonal Antibodies Specific to RSV F-Protein and Methods for their Manufacture and Therapeutic Use Thereof," U.S. Pat. Nos. 5,939,068 (1999) and 5,811,524 (1998)) describe methods for producing antibodies against the RSV F protein, and describe several antibodies developed using these methods.

Gurunathan et al., ("CD40 Ligand/Trimer DNA Enhances Both Humoral and Cellular Immune Response and Induces Protective Immunity to Infectious and Tumor Challenge," J. Immunol. 161, 4563 (1998)), describes the use of plasmids encoding a protein containing the CD40L coding region fused to a leucine zipper motif, called the CD40 ligand/trimer, to enhance Th1 and cytotoxic T-lymphocyte responses.

Alderson et al., ("Method for Stimulating an Immune Response," WO96/26735 (1996)), describes the use of a soluble, trimer-forming fragment of CD40L to enhance production of interleukin 12 in vitro, and to treat infection with Leishmania or Pneumocystis in CD40L-deficient mice.

The current invention provides adjuvants and methods that utilize a source of a CD40 binding protein, such as a vector operatively linked to CD40L, to enhance an immune response, especially a Th1 cytokine immune response, to an RSV vaccine.

SUMMARY OF THE INVENTION

The current invention discloses methods and adjuvants that utilize a source of a CD40 binding protein for enhancing an immune response to RSV.

A general embodiment of the current invention is a method for enhancing an immune response to respiratory syncytial virus (RSV), wherein an effective amount of an RSV vaccine and an effective amount of a source of a CD40 binding protein is administered to the host. Preferably, the CD40 binding protein is selected from the group consisting of CD40 ligand, CD40 ligand homologues, monoclonal antibodies that specifically bind CD40, and combinations thereof. Most preferably, the CD40 binding protein is CD40 ligand.

A preferred source of CD40 ligand, is a vector comprising a promoter operatively linked to nucleic acids encoding the CD40 ligand. Preferably the vector is a plasmid or an adenovirus vector.

In another embodiment of the method for enhancing an immune response wherein the CD40 binding protein is CD40 ligand, the host is a human whose genome comprises a mutated or a wild type CD40 ligand gene. In another embodiment of the method of enhancing an immune response wherein the CD40 binding protein is CD40 ligand, the RSV vaccine is selected from a vaccine comprising an RSV F gene product or a vaccine comprising a vector comprising a nucleic acid sequence encoding the RSV F gene product. In another embodiment of the method of enhancing an immune response wherein the CD40 binding protein is CD40 ligand, the RSV vaccine is selected from a vaccine comprising an RSV G gene product or a vaccine comprising a vector comprising a nucleic acid sequence encoding the RSV G gene.

In another embodiment of the method of enhancing an immune response wherein the CD40 binding protein is CD40 ligand, the immune response comprises a Th1 cytokine immune response. The phrase "Th1 cytokine immune response" as used herein refers to an increase in expression of IFNγ or IFN-2 by T-cells. In another embodiment the immune response comprises an antibody response.

In another general embodiment, the current invention comprises an adjuvant for enhancing an immune response of a host to respiratory syncytial virus (RSV) vaccination comprising an effective amount of a source of a CD40 binding protein. Preferably, the CD40 binding protein provided by the source is selected from the group consisting of CD40 ligand, CD40 ligand homologues, monoclonal antibodies that specifically bind CD40, and combinations thereof. More preferably, the CD40 binding protein is CD40 ligand. In this more preferred embodiment, the host is preferably a human.

In another embodiment, the source of CD40 ligand is a vector comprising a promoter operatively linked to nucleic acids encoding the CD40 ligand. In yet another embodiment, the vector in the adjuvant is a plasmid or an adenovirus vector.

In one preferred embodiment, the invention is an adjuvant for enhancing a Th1 immune response to an RSV antigen of a host that has a wild type CD40 ligand gene, wherein the adjuvant comprises an effective amount of an adenovirus vector comprising the cytomegalovirus (CMV) promoter operatively linked to nucleic acids encoding CD40 ligand.

In another general embodiment, the invention is a method for immunizing a host against disease caused by infection with respiratory syncytial virus (RSV), wherein the method comprises administering to the host, an effective amount of an RSV vaccine and an effective amount of a vector comprising a promoter operatively linked to nucleotide sequences encoding CD40 ligand. Preferably, the host is a human.

In still another embodiment of the general method for immunizing the host, the RSV vaccine is selected from a vaccine comprising an RSV F gene product or a vaccine comprising a vector comprising a nucleic acid sequence encoding the RSV F gene product. In another embodiment, the RSV vaccine is selected from a vaccine comprising an RSV G gene product or a vaccine comprising a vector comprising a nucleic acid sequence encoding the RSV G gene product.

In another preferred embodiment of the general method for immunizing the host, the vector is a plasmid. In another preferred embodiment, the vector is an adenovirus vector.

BRIEF DESCRIPTION OF THE DRAWINGS

FIG. 6. is a bar graph of RSV-specific antibody titers in sera from DNA-immunized mice challenged one week after the last immunization with RSV. Mice were immunized intradermally each week for 3 weeks using plasmid-coated gold beads administered by gene gun. Mice were immunized singly or in combination with plasmid DNA vectors that encoded F or G subunits or CD40L and subsequently challenged intranasally with $10^6$ pfu of RSV/A2. Sera were collected 2 weeks post RSV challenge and examined by ELISA for anti-RSV antibody titers. The data are expressed as ratios of the absorbance values for RSV-infected Vero cell lysates divided by uninfected Vero cell lysates. The results shown are the mean absorbance ratios for serum at a serum dilution of 1:3200 from 5-6 mice.

DESCRIPTION OF THE PREFERRED EMBODIMENTS

Figure 1A:
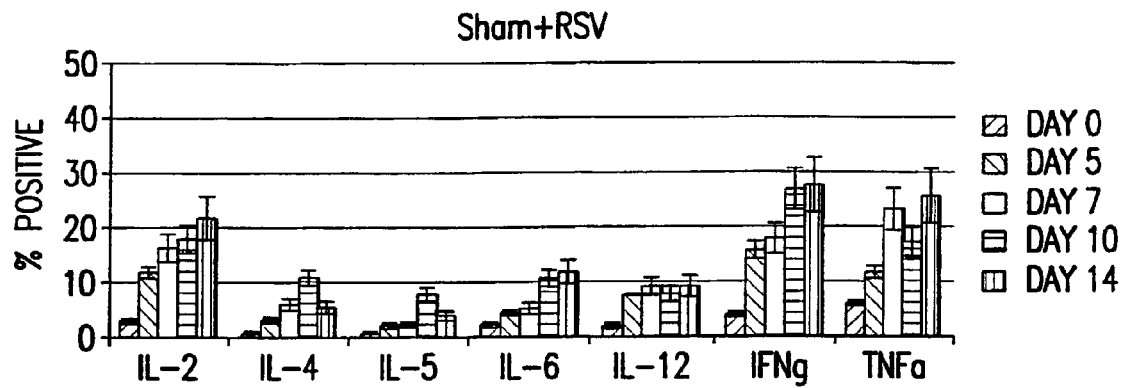
FIG. 1 is a series of bar graphs of the kinetics of intracellular cytokine expression by $CD3^+$ T lymphocytes isolated from the BAL after simultaneous intranasal infection with RSV and i.p administration of saline (sham-treatment) (FIG. 1A), or Ad-VC (FIG. 1B), or Ad-CD40L (FIG. 1C). The data for each time point is given as the mean percent of cells positive for the respective IC cytokine plus SEM of 4-6 individual mice.

CD40 Binding Proteins. The current invention includes methods and adjuvants for enhancing an immune response to a vaccine for respiratory syncytial virus (RSV) and, that utilize a source of a CD40 binding protein. The phrase "immune response" as used herein refers to a cell-mediated (cellular immunity) or antibody-mediated (humoral immunity) response of the immune system of a host. As used herein, the term "host" refers to a mammal. Methods for detecting and measuring an immune response are known to those skilled in the art. Some of these methods are illustrated in the examples found herein. As used herein the phrase "CD40 binding protein" refers to a protein that selectively binds to human CD40 antigen (CD40). As used herein, the term "selectively binds to" CD40, refers to the ability of proteins used in the present invention to preferentially bind to human CD40 antigen (CD40). Human CD40 antigen is a peptide of 277 amino acids having a molecular weight of 30,600 (Stamenkovic et al., *EMBO J.* 8:1403, (1989)). Methods are known in the art for detecting the selective binding of a protein to CD40. CD40 binding proteins include CD40L, homologues of CD40L, mimotopes of CD40L and monoclonal antibodies that selectively bind to CD40.

As used herein, CD40L refers to full-length CD40L found in a mammalian species. Preferred are murine and human CD40L. Especially preferred are human CD40L. Human CD40L, a membrane-bound glycoprotein, has been cloned from peripheral blood T-cells as described in Spriggs et al., *J. Exp. Med.* 176:1543 (1992). The cloning of murine CD40L is described in Armitage et al., *Nature* 357:80, 1992. A murine CD40L cDNA is described in Dilloo et al., "CD40 Ligand Induces an Antileukemia Immune Response In Vivo," *Blood* 90:1927 (1997).

Preferably, the CD40L used in the present invention is from the same species as the host to which it is administered to enhance an immune response. Human CD40L cDNA is predicted to encode a polypeptide of 261 amino acids comprising a 22 amino acid cytoplasmic domain, a 24 amino acid transmembrane domain, and a 215 amino acid extracellular domain with five cysteines (Banchereau et al. "The CD40 Antigen and Its Ligand," *Annu Rev. Immunol.* 12:881 (1994). The murine CD40L cDNA is predicted to encode a polypeptide of 260 amino acids comprising a 22 amino acid cytoplasmic domain, a 24 amino acid transmembrane domain, and a 214 amino acid extracelluar domain with four cysteines (Banchereau et al. (1994)). CD40L is a type II membrane polypeptide having an extracellular region at its C-terminus, a transmembrane region and an intracellular region at its N-terminus.

As used herein, a homologue of CD40L can include any portion (i.e. fragment) of CD40L, with or without modifications, or a modified full length CD40L, provided that the protein shares structural similarity with CD40L in the CD40 binding region and is capable of binding to CD40 and enhancing an immune response. When the homologue is administered to an animal as an adjuvant, using techniques known to those skilled in the art, the animal will produce an enhanced immune response against immunization with an RSV vaccine. Examples of CD40L homologues include CD40L proteins in which amino acids have been deleted (e.g., a truncated version of the protein, such as a peptide), inserted, inverted, substituted, and/or derivatized (e.g., by glycosylation, phosphorylation, acetylation, myristoylation, prenylation, palmitoylation, amidation and/or addition of glycerophosphatidyl inositol). CD40L homologues include fusion proteins that contain structural motifs not found on CD40L, connected to full length CD40L, or connected to fragments of CD40L.

CD40L homologues can be the result of natural allelic variation or natural mutation. CD40L homologues can also be produced using techniques known in the art including, but not limited to, direct modifications to the protein or modifications to the gene encoding the protein using, for example, classic or recombinant DNA techniques to effect random or targeted mutagenesis.

CD40L homologues of the present invention can be fusion proteins that include all, or part of, CD40L attached to one or more fusion segments. Suitable fusion segments for use with the present invention include, but are not limited to, segments that can enhance a protein's stability, assist in purification of the protein (e.g., by affinity chromatography), or preferably, that facilitate interactions between proteins with a structurally similar segment (e.g. a leucine zipper motif). Fusion segments can be joined to amino and/or carboxyl termini of the CD40L-containing domain of the protein and can be susceptible to cleavage in order to enable straight-forward recovery of CD40L protein.

Fusion proteins are preferably produced by culturing a recombinant cell transformed with a fusion nucleic acid molecule that encodes a protein including the fusion segment attached to either the carboxyl and/or amino terminal end of a CD40L-containing domain. Examples of fusion segments include a metal binding domain (e.g., a poly-histidine segment); an immunoglobulin binding domain (e.g., Protein A; Protein G; T cell; B cell; Fc receptor or complement protein antibody-binding domains); a domain facilitating dimerization (e.g., a leucine zipper), a sugar binding domain (e.g., a maltose binding domain); and/or a "tag" domain (e.g., at least a portion of β-galactosidase, a strep tag peptide, a T7 tag peptide, a Flag™ peptide, or other domains that can be purified using compounds that bind to the domain, such as monoclonal antibodies). As used herein, the term "purified" in relation to CD40 binding proteins means that the proteins are of sufficient purity so that they may be employed, and will function properly, in the methods of the present invention, as well as in clinical, diagnostic, experimental or other procedures. Many procedures are known by those of ordinary skill in the art for purifying proteins.

Certain CD40L homologues are described in the prior art. For example, a soluble form of CD40L has been described which comprises an extracellular region of CD40L, or a fragment thereof (Alderson et al., (1996)). Preparation of a soluble CD40L/Fc fusion protein referred to as CD40L/FC2 has been reported which contains an eight amino acid hydrophilic Flag™ sequence, an IgG1 Fe domain, a linker sequence, and the extracellular region of human CD40L (Alderson et al., (1996)). This CD40L homologue is capable of forming oligomers and capable of inducing human B cell proliferation in the absence of any co-stimuli, and, in conjunction with the appropriate cytokine, induces the production of IgG, IgE, IgA and IgM.

Additionally, CD40L homologues have been disclosed that are capable of forming oligomers due to the presence of a leucine zipper. Alderson et al., 1996, suggests a soluble CD40L fusion protein referred to as trimeric CD40L, which contains a 33 amino acid leucine zipper motif, the eight amino acid hydrophilic Flag™ sequence, followed by the extracellular region of human CD40L. Gurunathon et al., 1998 describes the preparation of a CD40L homologue comprising murine CD40L fused to an IL-7 leader and a leucine zipper sequence, designated CD40 ligand/trimer. These CD40L homologues capable of forming oligomers have been reported to be active at enhancing immunological responses.

CD40 binding proteins of the present invention also include mimotopes of CD40L. As used herein, a mimotope of CD40L refers to any compound that is capable of binding to CD40. Such mimotopes generally have structures similar to a portion of CD40L. Mimotopes can be, but are not limited to, peptides that have been modified to decrease their susceptibility to degradation such as all-D retro peptides; anti-idiotypic and/or catalytic antibodies, or fragments thereof; non-proteinaceous immunogenic portions of an isolated protein (e.g., carbohydrate structures); and synthetic or natural organic molecules, including nucleic acids. Such mimotopes can be designed using computer-generated structures of CD40 binding proteins of the present invention. Mimotopes can also be obtained by generating random samples of molecules, such as oligonucleotides, peptides or other organic molecules, and screening such samples by affinity chromatography techniques for binding to CD40L.

CD40 binding proteins of the present invention include monoclonal antibodies that selectively bind to CD40 (CD40 mAb). CD40 mAbs have been described and shown to mediate various biological activities on human B cells (Barrett et al., "CD40 signaling activates CD11a/CD18 (LFA-1)-mediated adhesion in B cells," *J. Immunol.* 146: 1722, 1991; Gordon et al., "Resting B lymphocytes can be triggered directly through the CDw40 (Bp50) antigen. A comparison with IL-4-mediated signaling," *J. Immunol.* 140:1425, 1988; Valle et al., "Activation of human B lymphocytes through CD40 and interleukin 4," *Eur. J. Immunol.* 19: 1463, 1989; Clark et al., "Activation of human B cells mediated through two distinct cell surface differentiation antigens, Bp35 and Bp50," *Proc. Natl. Acad. Sci. USA* 83:4494, 1986; Paulie et al., "The human B lymphocyte and carcinoma antigen, CDw40, is a phosphoprotein involved in growth signal transduction," *J. Immunol.* 142:590, 1989; Jabara et al., "CD40 and IgE: synergism between anti-CD40 monoclonal antibody and interleukin 4 in the induction of IgE synthesis by highly purified human B cells," *J. Exp. Med.* 172:1861, 1990; Gascan et al., "Anti-CD40 monoclonal antibodies or CD4+ T cell clones and IL-4 induce IgG4 and IgE switching in purified human B cells via different signaling pathways," *J. Immunol.* 147:8, 1991; Cairns et al., "Soluble CD23 is released by B lymphocytes cycling in response to interleukin 4 and anti-Bp50 (CDw40)," *Eur. J. Immunol.* 18:349, 1988; Clark et al., "Association between IL-6 and CD40 signaling. IL-6 induces phosphorylation of CD40 receptors," *J. Immunol.* 145: 1400, 1990). Additionally, CD40 mAbs are available through the American Type Culture Collection ((HB-11339, HB-11340, HB-12024), ATCC, Manassas, Va.). Additional CD40 monoclonal antibodies may be generated using conventional techniques (see e.g., U.S. Pat. No. RE 32,011; U.S. Pat. Nos. 4,902,614; 4,543,439; and 4,411,993; see also Antibodies: A Laboratory Manual, Harlow and Lane (eds.), Cold Spring Harbor Laboratory Press, 1988).

CD40 binding proteins may also be constructed utilizing recombinant DNA techniques to incorporate the variable regions of a gene which encodes an antibody to CD40. (See e.g., James W. Larrick et al., "Polymerase chain reaction using mixed primers: Cloning of human monoclonal antibody variable region genes from single hybridoma cells," *Biotechnology* 7:934-938, September 1989; Reichmann et al., "Reshaping human antibodies for therapy," *Nature* 332: 323-327, 1988; Roberts et al., "Generation of an antibody with enhanced affinity and specificity for its antigen by protein engineering," *Nature* 328:731-734, 1987; Verhoeyen et al., "Reshaping human antibodies: Grafting an antilysozyme activity," *Science* 239:1534-1536, 1988; Chaudhary et al., "A recombinant immunotoxin consisting of two antibody variable domains fused to *Pseudomonas exotoxin*," *Nature* 339:394-397, 1989).

Sources of CD40 Binding Proteins. The current invention includes method and adjuvants for enhancing an immune response to a vaccine for respiratory syncytial virus (RSV) that utilize an effective amount of a source of a CD40 binding protein. The source of a CD40 binding protein may comprise a CD40 binding protein or preferably a vector wherein a promoter is operatively linked to nucleic acids comprising the coding region of the CD40 binding protein. As used herein the term "vector" refers to a DNA delivery vehicle. As used herein the term "promoter" refers to a region of DNA involved in binding of RNA polymerase to initiate transcription. The phrase "operatively linked" as used herein refers to insertion of a nucleic acid coding sequence into a vector in a manner such that a promoter of the vector initiates expression of the coding sequence inside a host cell.

The phrase "effective amount" as used herein with respect to a source of a CD40 binding protein means that amount of the source of CD40L which is effective for enhancing an immune response to a challenge with RSV or an RSV vaccine. The phrase "effective amount" as used herein with respect to an RSV vaccine means that amount of an RSV vaccine that is effective for eliciting an immune response against RSV or an antigen of RSV.

The vector may be any vector capable of delivering a nucleic acid molecule into a host cell. Such a vector contains heterologous nucleic acid sequences, (i.e., nucleic acid sequences that are not naturally found adjacent to CD40 binding protein coding sequences and that preferably are derived from a species other than the species from which the CD40 binding protein coding sequences are derived). The vector can be either RNA or DNA, either prokaryotic or eukaryotic, and typically is a virus or a plasmid.

A preferred vector of the current invention is a recombinant vector comprising a CD40 binding protein coding region operatively linked to a promoter. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in mammalian cells.

In particular, expression vectors of the present invention contain regulatory sequences such as transcription control sequences, translation control sequences, origins of replication, and other regulatory sequences that are compatible with the host cell and that control the expression of nucleic acid molecules of the present invention. In particular, recombinant molecules of the present invention include transcription control sequences. Transcription control sequences are sequences which control the initiation, elongation, and/or termination of transcription. Particularly important transcription control sequences are those which control transcription initiation, such as promoter sequences. Suitable transcription control sequences include any transcription control sequence that can function in a mammalian cell. A variety of such transcription control sequences are known to those skilled in the art, including, but not limited to, the cytomegalovirus promoter, the Rous sarcoma virus promoter, the SV40 promoter, the EF-1α promoter, the UBC promoter, and the SG (sindbis) promoter. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences associated with CD40L.

Coding sequences for CD40 binding proteins used in recombinant vectors of the present invention can be continuous with sequences encoding secretory signals (i.e., signal segment nucleic acid sequences) to enable an expressed CD40 binding protein of the present invention to be secreted from the cell that produces the protein, and/or fusion sequences which lead to the expression of nucleic acid molecules of the present invention as fusion proteins. Examples of suitable signal segments include, but are not limited to, any signal segment capable of directing the secretion of a protein of the present invention. Preferred signal segments include secretion signal segments from tissue plasminogen activator (t-PA), interferon, interleukin, growth hormone, histocompatibility, and viral envelope glycoproteins. Suitable fusion segments encoded by fusion segment nucleic acids include, but are not limited to, a metal binding domain (e.g., a poly-histidine segment); an immunoglobulin binding domain (e.g., Protein A; Protein G; T cell; B cell; Fc receptor or complement protein antibody-binding domains); a domain facilitating dimerization (e.g., a leucine zipper), a sugar binding domain (e.g., a maltose binding domain), and/or a "tag" domain (e.g., at least a portion of β-galactosidase, a strep tag peptide, a T7 tag peptide, a Flag™ peptide, or other domains that can be purified using compounds that bind to the domain, such as monoclonal antibodies).

Coding sequences for CD40 binding proteins have been described in the art. For example, cDNAs encoding the mouse and human CD40L proteins have been described, as discussed above. As used herein, the term "coding region" refers to a continuous linear array of nucleotides that translates into a protein. A full-length coding region is that coding region that is translated into a full-length (i.e., complete) protein as would be initially translated in its natural milieu, prior to any post-translational modifications. Preferably, in the current invention the CD40 binding protein coding region is a full-length mouse or human CD40L coding region.

In accordance with the present invention, an isolated nucleic acid molecule is a nucleic acid molecule that has been removed from its natural milieu (i.e., that has been subjected to human manipulation) and can include DNA, RNA, or derivatives of either DNA or RNA. As such, "isolated" does not reflect the extent to which the nucleic acid molecule has been purified. An isolated nucleic acid molecule of the present invention encoding a CD40 ligand binding protein, including a homologue thereof, can be isolated from its natural source or produced using recombinant DNA technology (e.g., polymerase chain reaction (PCR) amplification or cloning) or chemical synthesis. Examples of isolated nucleic acid molecules encoding CD40 binding proteins include a nucleic acid molecule encoding CD40L as well as homologues thereof, such as natural allelic variants, and nucleic acid molecules modified by nucleotide insertions, deletions, substitutions, and/or inversions of any of the foregoing nucleic acid molecules in a manner such that the modifications do not substantially interfere with the nucleic acid molecule's ability to encode a CD40 binding protein of the present invention.

As used herein, an allelic variant of a CD40L gene is a gene that occurs at essentially the same locus (or loci) in the genome as the CD40L gene, but which, due to natural variations caused by, for example, mutation or recombination, has a similar but not identical sequence. Allelic variants of genes or nucleic acid molecules can also comprise alterations in the 5' or 3' untranslated regions of the gene (e.g., in regulatory control regions), or can involve alternative splicing of a nascent transcript, thereby bringing alternative exons into juxtaposition. As described above, some non-functional allelic variants are known to occur in the human CD40L gene.

CD40 binding proteins utilized in the methods and adjuvants of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. Effective culture conditions include, but are not limited to, media, bioreactor, temperature, pH and oxygen conditions that permit protein production. Suitable media are any media in which cells can be cultured to produce a CD40 binding protein of the present invention. Such medium typically comprises an aqueous medium having assimilable carbon, nitrogen, and phosphate sources, and appropriate salts, minerals, metals and other nutrients (e.g., vitamins). To produce CD40 binding proteins utilized in the present invention, cells can be cultured in conventional fermentation bioreactors, shake flasks, test tubes, microtiter dishes, Petri plates, and the like. Culturing can be carried out at temperatures, pHs and oxygen contents appropriate for a recombinant cell. Such culturing media and conditions are within the expertise of one of ordinary skill in the art.

The phrase "recovering the protein", as well as similar phrases, refers to collecting the whole fermentation medium containing the protein and can (but is not required) involve additional steps of separation and/or purification. CD40 binding proteins used in the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing, and differential solubilization.

CD40 binding proteins used in the present invention are preferably retrieved in "substantially pure" form. As used herein, "substantially pure" refers to a purity that allows for the effective use of the protein to enhance an immunological response. For example, the protein should exhibit no substantial toxicity.

Hosts. The host of the methods and adjuvants of the current invention is a mammal. Typically, the host is a mouse or a human, preferably a human. Mice and humans having defective CD40 ligand genes have been described (Hill et al. "X-Linked Immunodeficiency—The Fruits of Cooperation," *Nature* 361:494 (1993); Arufo et al. "The CD40 Ligand, gp39, Is Defective in Activated T cells from Patients with X-Linked Hyper-IgM Syndrome," *Cell* 82:291 (1993); Allen et al., "CD40 Ligand Gene Defects Responsible for X-Linked Hyper-IgM Syndrome," *Science* 259:990 (1995); Castigli et al. (1994)). For example, humans suffering from X-linked hyper-IgM syndrome have mutations of their CD40L gene. Transgenic mice have been described that do not possess a functional copy of a CD40L gene (Castigli et al. (1994)).

RSV Vaccines. The current invention comprises methods that utilize RSV vaccines and adjuvants that enhance the effectiveness of such vaccines. Many RSV vaccines are known in the art, including inactivated virus, live-attenuated viruses, and subunit vaccines comprising either the subunit itself or a DNA molecule encoding a subunit protein. Subunit vaccines have been described that comprise the RSV F protein and the RSV G protein (Groothuis et al., (1998); Neuzil et al., (1997); and Siegrist et al., (1999)). Additionally, a vaccine comprising a vector expressing an RSV F protein has been disclosed (Li et al., (1999)). Any RSV vaccine could be used with the current invention provided that the vaccine elicits an immune response against RSV when it is used in conjunction with a CD40 binding protein.

Preparation and Administration of Sources of CD40 Binding Proteins. The methods and adjuvants of the current invention involve preparation and administration of sources of a CD40 binding protein. In a preferred embodiment the source is a recombinant vector. The recombinant vector is administered to an animal in a fashion to enable expression in the animal of a CD40 binding protein coding region of that recombinant vector. Nucleic acid molecules can be delivered to an animal in a variety of methods including, but not limited to, (a) administering a naked (i.e., not packaged in a viral coat or cellular membrane) nucleic acid (e.g., as naked DNA or RNA molecules, such as is taught, for example, in Wolff et al., 1990, *Science* 247, 1465-1468) or (b) administering a nucleic acid molecule packaged as a recombinant virus or as a recombinant cell (i.e., the nucleic acid molecule is delivered by a viral or cellular vehicle).

A recombinant vector of the present invention can comprise a recombinant virus that is packaged in a viral coat and that can be expressed in an animal after administration. Preferably, the recombinant virus is packaging- or replication-deficient and/or encodes an attenuated virus. A number of recombinant viruses can be used, including, but not limited to, those based on alphaviruses, poxviruses, adenoviruses, herpesviruses, picornaviruses, and retroviruses. In one preferred embodiment, the recombinant virus is a recombinant adenovirus. In another preferred embodiment, the recombinant virus is an avipox virus, preferably a canarypox virus, such as, but not limited to ALVAC, or a fowlpox virus, such as, but not limited to TROVAC. (Perkus et al., "Poxvirus-based vaccine candidates for cancer, AIDS, and other infectious diseases," *Journal of Leukocyte Biology* 58:1 (1995)).

In one embodiment, the recombinant virus can be used to co-deliver both the CD40 binding protein and an RSV vaccine, such as, but not limited to, the RSV F gene product. Successful co-delivery of a vaccine and a cytokine using a viral vector has been reported (Leong et al., "Selective induction of immune responses by cytokines coexpressed in recombinant fowlpox virus," *Journal of Virology* 68:8125 (1994); Ramsay et al., "Enhancement of mucosal IgA responses by interleukins 5 and 6 encoded in recombinant vaccine vectors," *Reproduction, Fertility and Development* 6:389 (1994); Ramshaw et al., "Recovery of immunodeficient mice from a vaccinia virus/IL-2 recombinant infection," *Nature* 329:545 (1987).

Whether a recombinant vector or a protein, the source of CD40 binding protein of the present invention can be formulated in an excipient that the animal to be treated can tolerate. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides can also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, and the like, to which sterile water or saline can be added prior to administration.

In one embodiment of the present invention, the CD40 binding protein source is administered along with a carrier. Carriers include compounds that increase the half-life of the CD40 binding protein source in the treated animal. Suitable carriers include, but are not limited to, polymeric controlled release vehicles, biodegradable implants, liposomes, bacteria, viruses, other cells, oils, esters, glycols, and the like.

One embodiment of the present invention is a controlled release formulation or vehicle that is capable of controllably and/or slowly releasing a composition of the present invention into an animal. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Other controlled release formulations of the present invention include liquids that, upon administration to an animal, form a solid or a gel in situ. Preferred controlled release formulations are biodegradable or bioerodible.

Whether the source of a CD40 binding protein is a vector or the protein itself, the source can be administered to animals prior to administration of an RSV vaccine, after administration of the RSV vaccine, or simultaneously with administration the RSV vaccine. Acceptable protocols to administer CD40 binding protein sources in a effective manner include individual dose size, number of doses, frequency of dose administration, and mode of administration. Determination of such protocols can be accomplished by those skilled in the art.

A suitable single dose is a dose that is capable of enhancing an immune response to an RSV vaccine. For example, a preferred single dose of a CD40 binding protein is from about 1 microgram (µg) to about 10 milligrams (mg) of the CD40 binding protein per kilogram body weight of the animal. A preferred single dose of a recombinant vector ranges from about 1 nanogram (ng) to about 600 µg for a plasmid vector, or from about $1 \times 10^4$ to about $1 \times 10^8$ virus plaque forming units (pfu) per kilogram body weight of the animal. The effective dose rates may be influenced by the route of administration and/or method of delivery; such variation can be determined by those skilled in the art.

The source of a CD40 binding protein can be administered in a variety of ways, with intramuscular, subcutaneous, intradermal, transdermal, intranasal, and oral routes of administration being preferred. Suitable delivery methods include, for example, injection, drops, aerosolized, and/or topical application. In one embodiment where the source of a CD40 binding protein is a plasmid, the recombinant plasmid can be administered using the Helios Gene Gun (BioRad, Hercules, Calif.). If such a gene gun is used, the recombinant plasmid is first precipitated onto 1-micron gold microcarriers according to the manufacturer's instructions (BioRad, Hercules, Calif.).

The following examples describe and illustrate the methods and compositions of the invention. These examples are intended to be merely illustrative of the present invention, and not limiting thereof in either scope or spirit. Those of skill in the art will readily understand that variations of the materials used in, and the conditions and processes of, the procedures described in these examples can be used.

EXAMPLE 1

CD40L Enhances the Expression of Intracellular Th1 Cytokines

Cytokine expression was analyzed in T cells of the spleen and the bronchoalveolar lavage (BAL) after concurrently infecting mice intranasally with RSV and treating the mice with an adenovirus vector expressing CD40L. Four-to-six week old, specific-pathogen free, female BALB/c mice (Harlan Sprague Dawley Laboratories, Indianapolis, Ind.) were anesthetized with Avertin and subsequently infected by intranasal administration of $10^6$ pfu/mouse of A2 immediately followed by intraperitoneal infection with $2 \times 10^7$ pfu/mouse with either adenovirus construct Ad-VC, Ad-CD40L (as described below) or a PBS control (sham). At various time points post-infection mice were anesthetized with Avertin and exsanguinated by severing the right caudal artery; lymphoid organs and cells were then removed. All organs and cells were collected on ice in Hank's Balanced Salt Solution (HBSS, GIBCO). The lung was lavaged 3× using HBSS containing 1.0% bovine serum albumin (BSA, Sigma). Four-to-six mice were used for each experiment and each experiment was repeated three times. Sample variance ($s^2$) and SEMs were calculated using standard statistical formulae.

For flow cytometric analysis of cytokine expression, single cell suspensions of lymphocytes were blocked with 10% normal mouse sera (Jackson Laboratories, Bar Harbor, Me.) in D-PBS for 15 min at 4° C. The procedure used for intracellular (IC) cytokine staining was modified for microculture staining from the protocol described by PharMingen. Briefly, the cells were washed in PBS (GIBCO), and the cell surface antigen was stained with the appropriate antibody and subsequently fixed with 4% paraformaldehyde (Ted Pella Inc., Redding, Calif.) in D-PBS containing 1.0% BSA. The cells were washed in PBS and the membranes were permeabilized using 0.1% saponin (Sigma). Antibodies were PE-labeled and purchased from PharMingen. Anti-IL-2

(JES6-5H4), anti-IL-4 (BVD4-1D11), anti-IL-5 (TRFK5), anti-IL-6 (MP5-20F3), anti-IL-12 (C15.6), anti-IFNγ (XMG1.2) and anti-TNFα (MP6-XT22) Ab were diluted in D-PBS containing 0.1% BSA and 0.1% saponin. The cells were stained on ice for 30 min, using appropriate dilutions of the antibody, washed, resuspended in D-PBS containing 1.0% BSA, and analyzed using FACScan. A lymphocyte gate was used to analyze ≧10,000 events. The distribution of cell surface markers was determined in two-color mode on FACScan with CellQUEST software (Becton-Dickinson, Mountain View, Calif.).

For these experiments, RSV/A2 (A2) was prepared in the following manner: A2 was grown in Vero cells (African green monkey kidney fibroblasts (ATCC CCL 81) and maintained in RPMI 1640 (GIBCO laboratories, Grand Island, N.Y.) supplemented with 2% heat-inactivated (56° C. for 30 min) fetal bovine serum (FBS; Hyclone Laboratories, Salt Lake City, Utah), 1% L-glutamine and 1% antibiotic/antimycotic (TCM) (all from GIBCO). Upon visually detectable cytopathic effect, the medium was decanted and replaced with a minimal volume of Dulbecco's modified PBS (D-PBS) and frozen at −70° C. The flask was thawed and the loosely adherent cell monolayer scraped off using a cell scraper (Costar, Cambridge, Mass.) and collected. The cell lysate and supernatant were centrifuged at 2000 G for 20 min at 4° C. The resultant supernatants were collected, subdivided into aliquots, and stored at −70° C. or at liquid nitrogen temperatures. The titer was determined by methylcellulose plaque assay on Vero cells. Virus titer was measured by methylcellulose plaque assay. Virus stock was incubated for 3h incubation at 37° C. on a vero cell monolayer that was then overlaid with 2% carboxymethylcellulose (Sigma, St. Louis, Mo.) in TCM and incubated for 5-6 days at 37° C. Finally, the cells were fixed with 4% formalin containing 0.1% crystal violet dye (Sigma) and the endpoint titer was determined by macroscopic counting of plaques.

For these experiments recombinant adenovirus expressing CD40L were prepared in the following manner. The murine CD40L cDNA (SEQ ID NO:1)(Dilloo et al., "CD40 ligand induces an antileukemia immune response in vivo," *Blood* 90:1927 (1997)) was cloned into the XbaI and EcoRV sites of the pAVS6 adenoviral recombination plasmid (Genetic Therapy Inc., Gaithersburg, Md.) under the control of the cytomegalovirus promoter. Control (Ad-VC) and murine CD40L adenovirus vectors (Ad-CD40L) were produced using the procedure as described in Leimig et al., "High-efficiency transduction of freshly isolated human tumor cells using adenoviral interleukin-2 vectors," *Human Gene Therapy* 7:1233 (1996). The empty control adenovirus vector (Ad-VC) was produced under identical conditions except that it lacked murine CD40L cDNA insert. Virus titer was measured by plaque assay on 293 cells. Adenovirus vectors were rendered replication defective by triple plaque purification. Defective replication was confirmed by serial passage on A549 cells.

Figure 1B:
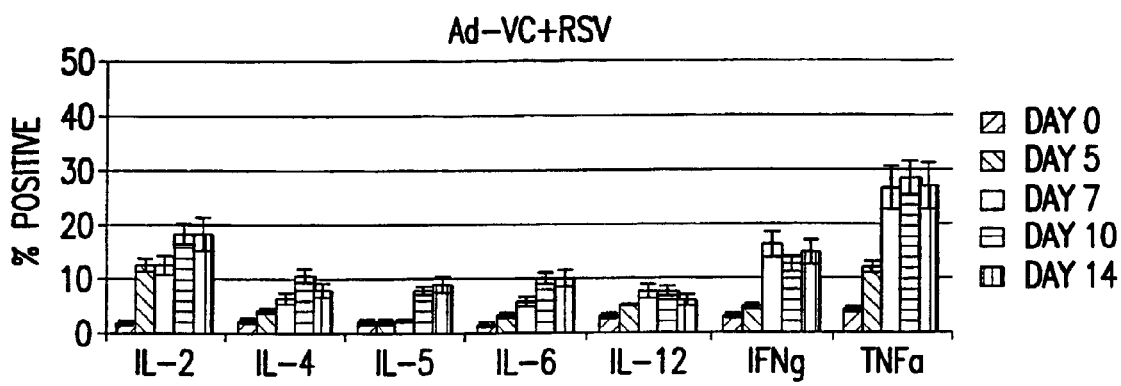
Figure 1C:
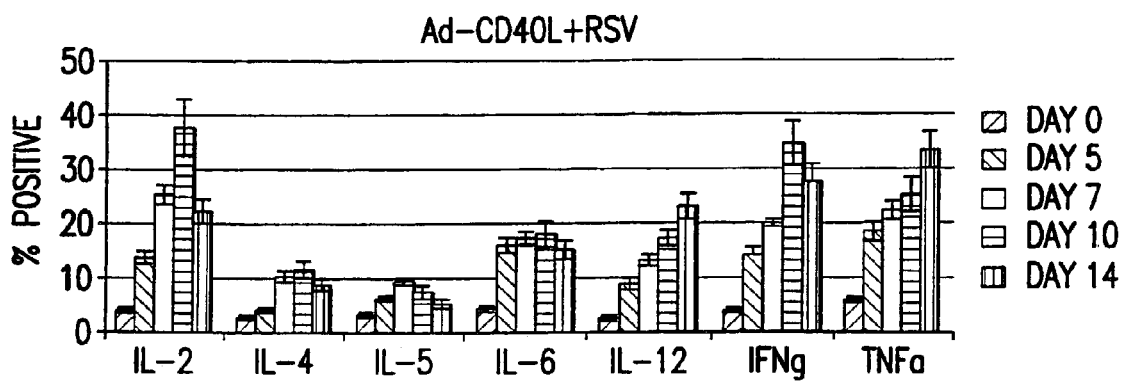

BALB/c mice infected intranasally with RSV were concurrently given saline (sham) treatment intraperitoneal (FIG. 1A) or infected with empty adenovirus vector, or with Ad-VC (FIG. 1B), or Ad vector containing the murine CD40L cDNA, Ad-CD40L (FIG. 1C). The kinetics of the intracellular (IC) cytokine response of T cells is shown in FIG. 1. BAL T cells from sham-treated mice after RSV challenge expressed peak cytokines between days 7 and 14 post-infection (FIG. 1A). Expression of Th1 cytokine levels was generally higher than Th2 cytokines (FIG. 1A). Following RSV infection, BAL T cells from mice infected with Ad-VC (FIG. 1B) showed a similar kinetics and patterns of cytokine expression as sham-treated mice (FIG. 1A). Peak expression levels of Th1 cytokines IL-2 (19%) and IFNγ (17%), were higher than those of Th2 cytokines, IL-4 (11%), IL-5 (9%), and IL-6 (10%) (FIG. 1B). In comparison, BAL T cells from mice simultaneously infected with Ad-CD40L and RSV had augmented expression levels of IL-2, IL-6, IL-12, IFNγ and TNFα and modified cytokine expression kinetics (FIG. 1C). Maximal expression levels of IL-2 expression (38%) occurred at day 10 post-infection; peak IL-6 expression (18%) at day 10 post-infection; peak IL-12 expression (25%) at day 14 post-infection; peak IFNγ expression (36%) at day 10 post-infection and peak TNFα expression (34%) at day 14 post-infection (FIG. 1C). Expression of IL-4 or IL-5 was not increased in comparison with either sham-treated (FIG. 1A) or Ad-VC-infected (FIG. 1B) mice, suggesting that coincident expression of CD40L primarily enhanced Th1-type cytokine expression.

Figure 2A:
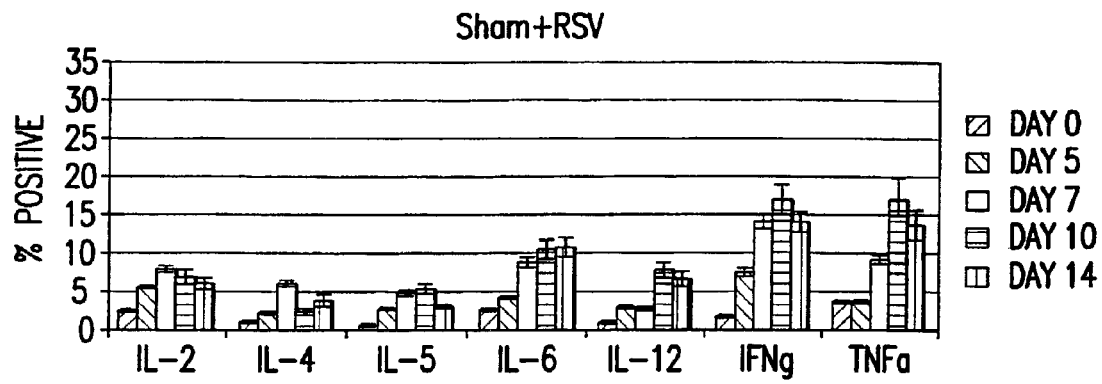
FIG. 2. is a series of bar graphs of the kinetics of intracellular cytokine expression by $CD3^+$ T lymphocytes isolated from the spleen after simultaneous intranasal infection with RSV and i.p administration of saline (sham-treatment) (FIG. 2A), or Ad-VC (FIG. 2B), or Ad-CD40L (FIG. 2C). The data for each time point is given as the mean percent of cells positive for the respective IC cytokine plus SEM of 4-6 individual mice.
Figure 2B:
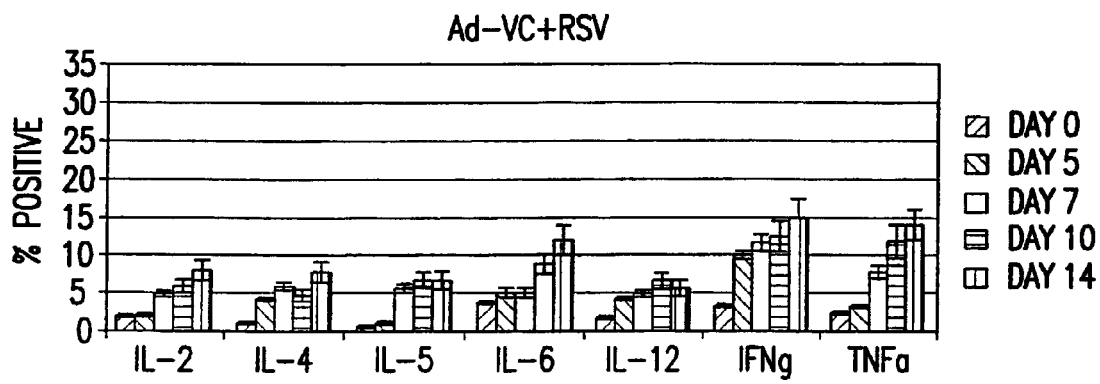
Figure 2C:
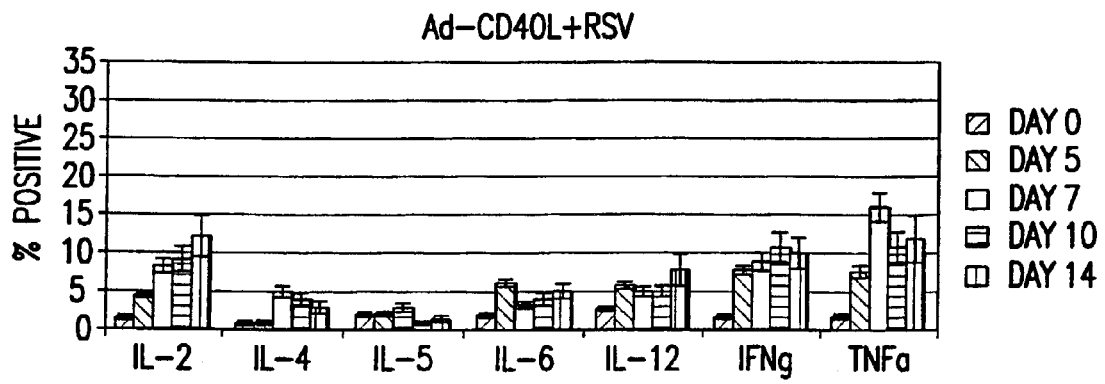

Cytokine expression in T cells from the spleen was also analyzed after Ad vector infection and RSV challenge (FIG. 2). Although, the percent of CD3$^+$ T cells positive for each cytokine increased post-treatment when compared to naïve (day 0) values, the percent of cells expressing each cytokine was lower in spleen than in BAL (FIG. 1). The Th1/Th2 cytokine profiles were similar to those observed in T cells from the BAL. Sham-treated mice that were infected with RSV alone maximally expressed Th1 (IL-2, IL-12, IFNγ) and Th2 (IL-4, IL-5, IL-6) cytokines and TNFα between day 7 and 10 post-infection (FIG. 2A). The cytokine profiles for Ad-VC infected (FIG. 2B) and sham-treated mice were similar except for a shift in the kinetics of the peak response. Peak cytokine expression for IL-2 (8%), IL-4 (8%), IL-6 (13%), IFNγ (15%) and TNFα (14%) all occurred at day 14 post-infection, whereas peak expression of IL-5 (6%) and IL-12 (7%) occurred at day 10 post-infection (FIG. 2B). Infection with Ad-CD40L lead to a decrease in the expression of Th2 cytokines and IFNγ (FIG. 2C).

EXAMPLE 2

CD40L Enhances the Secretion of Pulmonary Th1 Cytokines

An analysis was performed of the effect of treatment with adenoviruses expressing CD40L on cytokine secretion in the cell-free BAL fluid of RSV-infected mice. Infection of mice with recombinant viruses and collection of cells and organs was carried out as described in Example 1.

Secreted cytokines in BAL cell-free exudate were quantitated using FlowMatrix analysis (Luminex Corp., Austin, Tex.) and a FACScan (Becton-Dickinson) using a modified antibody capture-sandwich assay protocol on defined latex microspheres. In brief, individual pre-stained red spectrum-colored microsphere bead sets (Luminex) were diluted in PBS/Tween (Sigma). The capture antibodies (anti-IL-2; JES-1A12, anti-IL-4; BVD4-1D11, anti-IL-5; TRFK5 and anti-IFNγ; R4-6A2, all from PharMingen) were covalently coupled to the bead sets using a two-step method described by Luminex. Duplicate dilutions of recombinant murine IL-2, IL-4, IL-5, and IFNγ (Genzyme, Cambridge, Mass.) in PBS/Tween were used to generate a standard curve and were assayed against duplicate dilutions of cell-free BAL exudate in PBS. Capture antibody-coated microspheres were incubated with normalized 1-ml standards or unknown 1-ml samples for 30 minutes at room temperature. Following incubation, ALEXA-streptavidin (Molecular Probes, Eugene, Oreg.) conjugated, biotinylated cytokine detection antibodies (IL-2; JES6-5H4, IL-4; BVD6-24G2, IL-5; TRFK4, and IFNγ; XMG1.2, all from PharMingen) were incubated with the samples for 20 minutes at room temperature. Following incubation, the beads were pelleted by centrifugation, resuspended in PBS/TBN and analyzed using FACScan and FlowMatrix software.

Figure 3A:
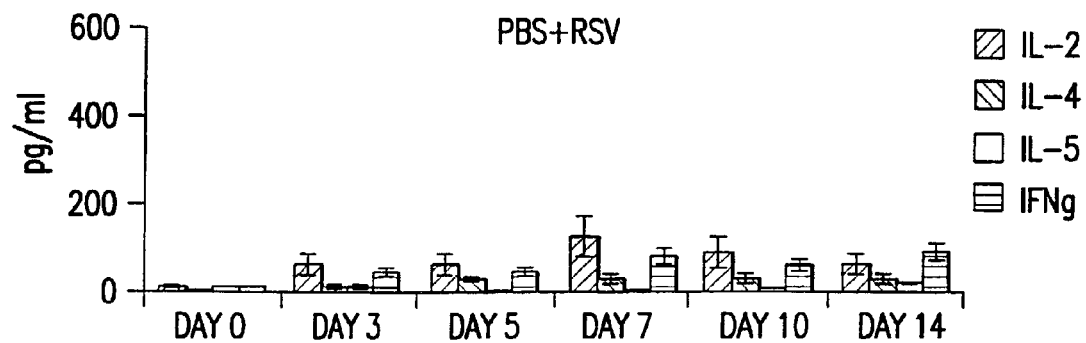
FIG. 3. is a series of bar graphs quantifying Th1 (IL-2, IFNγ) and Th2 (IL-4, IL-5) cytokine secretion in the cell-free BAL fluid during the immune response of mice treated simultaneously with RSV intranasal and intraperitoneal injections of saline (sham-treated) (FIG. 3A), or Ad-VC (FIG. 3B), or Ad-CD40L (FIG. 3C). The data for each time point is given as the mean pg/ml of the cytokine plus SEM of 4-6 individual mice.
Figure 3B:
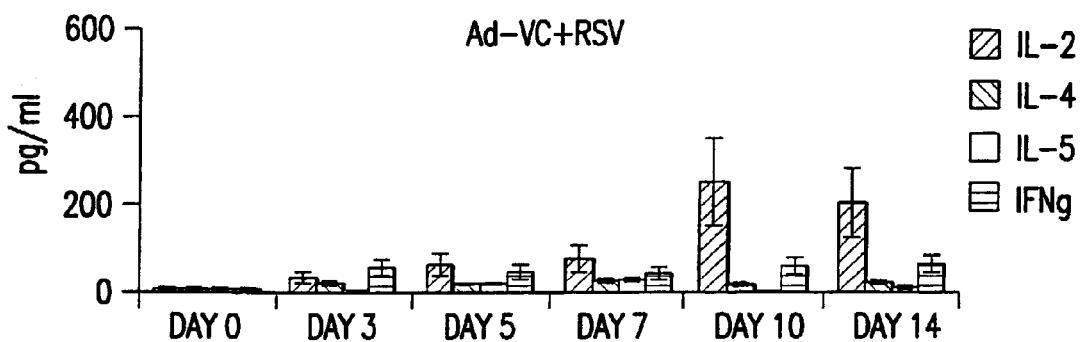
Figure 3C:
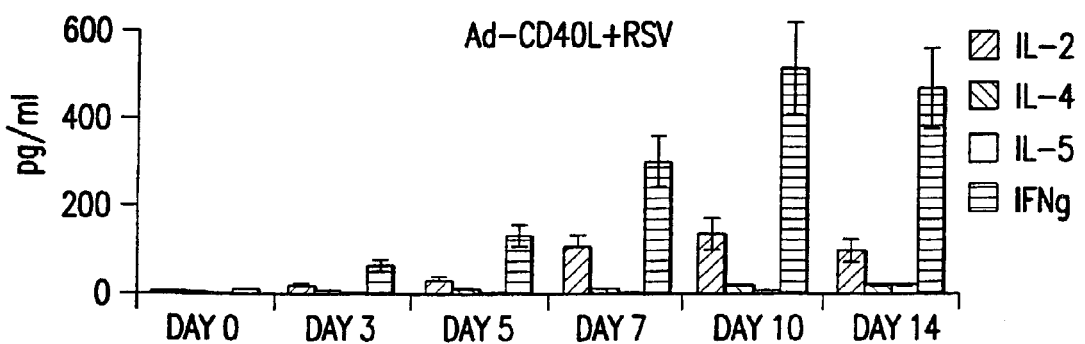

The concentrations of Th1 (IL-2, IFNγ) and Th2 (IL-4, IL-5) cytokines in the cell-free BAL fluid of RSV-infected, sham-treated mice (FIG. 3A), Ad-VC infected (FIG. 3B), or Ad-CD40L infected (FIG. 3C) mice were determined. The BAL cytokine response in sham-treated and Ad-VC-infected mice was moderate compared to Ad-CD40L infected mice. For sham-treated mice, IL-2 and IFNγ concentrations ranged from 50-100 pg/ml from days 3-14 post-infection and IL-4 and IL-5 ranged from 10-25 pg/ml (FIG. 3A). Similar concentrations of secreted cytokines were detected in Ad-VC infected mice (FIG. 3B), except that higher levels of IL-2 (200-225 pg/ml) were found between day 7 and 14 post-infection (FIG. 3B). The late elevation in IL-2 may reflect an anti-adenovirus T cell response occurring in the lung; Ad given intraperitoneal is expected to infect the lung. In contrast to Ad-VC associated cytokine levels, much higher levels of IFNγ were produced in BAL after infection with Ad-CD40L (FIG. 3C). In particular, 75-150 pg/ml of IL-2 and 150-300 pg/ml IFNγ were detected between days 5-7 post-infection that peaked at day 10 post-infection (IL-2, 175 pg/ml; IFNγ, 525 pg/ml;). IL-4 and IL-5 were not detected in the BAL at any time-point examined (FIG. 3C). These data suggest that infection with Ad-CD40L can enhance the Th1 cytokine response in the lung, especially augmenting the production of IFNγ.

EXAMPLE 3

Coincident Expression of CD40L Enhances Pulmonary Nitrite Production Associated with Enhanced Virus Clearance The effect of treatment with adenoviruses expressing CD40L on nitrite production in the cell-free BAL fluid of RSV-infected mice was evaluated in this experiment. Infection of mice with recombinant viruses and collection of cells and organs was carried out as described in Example 1.

Nitrite was measured by using a modified Greiss reaction. Briefly, 1 ml cell-free bronchoalveolar lavage (BAL) samples were diluted two-fold with distilled water and deproteinized by zinc sulfate to give a final concentration of 15 g/L. The samples were centrifuged at 1000G for 15 minutes at 10° C., and 0.1 ml aliquots were transferred to microtiter plate wells (Costar). 0.1 ml of Greiss reagent (1 g/L sulfanilamide, 25 g/L phosphoric acid, 0.1 g/L N-1-napthylethylenediamine) was added to the wells, mixed by gentle pipetting and allowed to incubate for 15 min at room temperature. The absorbance was read on a microplate reader (Titertek, McLean, Va.) at 540 nm. Each sample was assayed in triplicate. Background was determined by treating normalized BAL samples only with 25 g/L phosphoric acid. Sodium nitrite in distilled water was used to generate standard curves.

Figure 4:
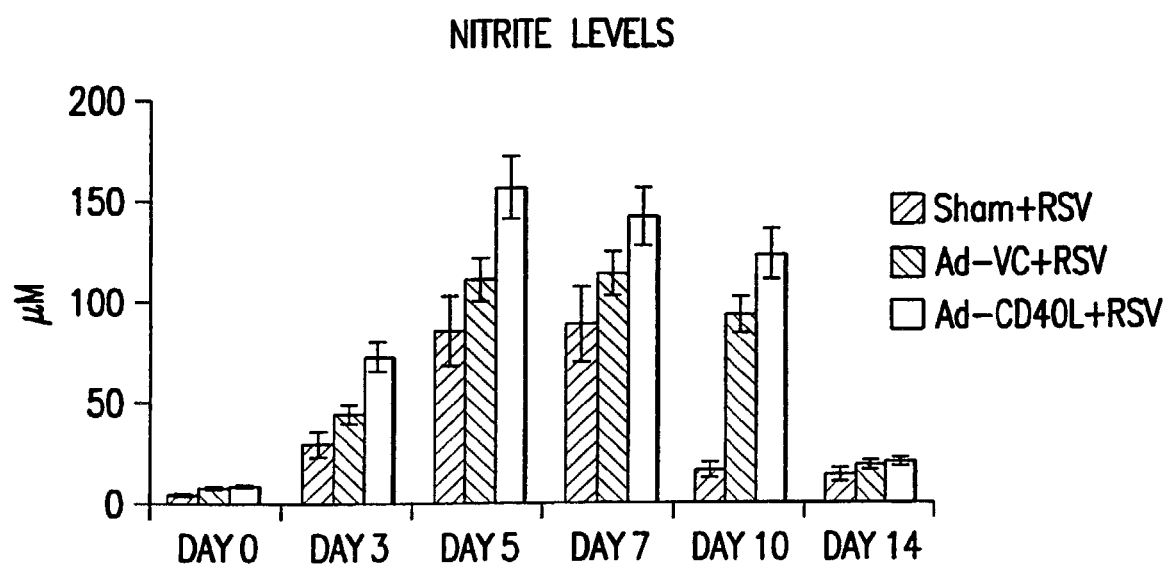
FIG. 4. is a bar graph of nitrite levels produced in the cell-free BAL of mice treated simultaneously with RSV and intraperitoneal injections of saline (sham-treated), or Ad-VC, or Ad-CD40L. The data for each time point is given as μM of nitrite plus SEM of 4-6 individual mice.

Titers of RSV in the lungs of mice were determined in the following manner: Vero cell monolayers were seeded onto 24-well flat-bottom tissue culture plates. Cells were inoculated with 200 µl of 10-fold dilutions of lung lysate in PBS. Virus was allowed to absorb for 2 h at 37° C., and overlay media was added to each well. Overlay media consisted of RPMI-1640+2% FCS+0.9% Noble agar. The cultures were incubated for 6-7 days at 37° C., fixed for 5 minutes with staining solution (PBS+1% glutaraldehyde+0.1% crystal violet) and individual plaques counted. Virus titers were determined from 3 replicates/dilution Pulmonary macrophages produce nitric oxide (NO) to destroy pathogens and invasive organisms. The NO reaction produces nitrite, molecular oxygen, and water; thus nitrite levels generally correlate with NO production (Chin et al., (1969)). Nitrite concentrations for sham-treated, Ad-VC-infected and Ad-CD40L-infected mice that challenged simultaneously with RSV are shown in FIG. 4. BAL nitrite levels peaked between day 5 and 7 post-infection in sham-treated (90 µM), Ad-VC-infected (125 µM) and Ad-CD40L-infected mice (160 µM) mice. By day 10 post-infection, BAL nitrite levels declined in sham-treated mice (25 µM), but remained high in Ad-VC-infected and Ad-CD40L-infected mice. By day 14 post-infection, nitrite levels had dropped to 20-35 µM range in all groups (FIG. 4).

Enhanced virus clearance was observed in mice infected with Ad-CD40L compared to sham-treated or Ad-VC-infected mice (Table 1). Ad-CD40L-infected mice challenged with RSV cleared virus by day 7 post-infection, whereas sham-treated and Ad-VC-infected mice cleared virus between day 10-14 post-infection. Moreover, Ad-CD40L-treated mice exhibited reduced RSV titers at day 6 post-infection, compared to sham-treated or Ad-VC-infected mice. The enhanced virus clearance correlated temporally with CD40L expression, increased pulmonary NO production and enhanced IC Th1 cytokines and pulmonary Th1 cytokine secretion.

TABLE 1

Titer of RSV in lungs of mice.

| Days p.i.[1] | Virus intraperitoneal | Virus intranasal | Log Virus Titer[2] |
|---|---|---|---|
| 3 | PBS | RSV | 5.0–6.5 |
| 3 | Ad-VC | RSV | 5.5–6.5 |
| 3 | Ad-CD40L | RSV | 5.0–6.0 |
| 5 | PBS | RSV | 3.5–5.0 |
| 5 | Ad-VC | RSV | 4.0–5.0 |
| 5 | Ad-CD40L | RSV | 4.0–5.0 |
| 6 | PBS | RSV | 3.0–4.5 |
| 6 | Ad-VC | RSV | 3.5–4.5 |
| 6 | Ad-CD40L | RSV | 2.0–3.0 |
| 7 | PBS | RSV | 3.0–4.0 |
| 7 | Ad-VC | RSV | 3.0–4.0 |
| 7 | Ad-CD40L | RSV | 0 |
| 10 | PBS | RSV | 1.0–2.0 |
| 10 | Ad-VC | RSV | 2.0–3.0 |
| 10 | Ad-CD40L | RSV | 0 |
| 14 | PBS | RSV | 0 |
| 14 | Ad-VC | RSV | 1.0–1.5 |
| 14 | Ad-CD40L | RSV | 0 |

[1]P.i. = post-infection
[2]Data represents range of dilution's producing plaques.

EXAMPLE 4

RSV-Specific MHC Class I-Restricted CTLp Frequencies Persist in CD40L Treated Mice The effect of treatment with recombinant adenoviruses expressing CD40L on MHC class I-restricted CTLp frequencies in the BAL of RSV-infected mice was evaluated. Infection of mice with recombinant viruses and collection of cells and organs was carried out as described in Example 1.

Class I-restricted target cells used were the mouse mastocytoma line, P815 (ATCC TIB 64). The P815 cell lines was maintained in RPMI 1640 (GIBCO) containing 10% FBS (Hyclone) plus 1% antibiotic/antimycotic (GIBCO). The target cells were prepared by suspending $10^6$ cells in 1.0 ml of serum-free MEM (GIBCO) containing $10^4$ pfu/ml RSV cell lysate (or comparable dilution of uninfected cell control lysate) for 18 h at 37° C. followed by addition of 1.0 ml of MEM containing 10% FBS and 200 µCi $^{51}$Cr (Na$_2$CrO$_4$, Amersham, Arlington Heights, Ill.), and incubating for an additional 2 h at 37° C. The cells were then washed and resuspended to an appropriate concentration in TCM comprised of S-MEM (GIBCO) containing 10% FBS (Hyclone), 1% essential amino acids, 2% nonessential amino acids, 2% sodium pyruvate, 2% L-glutamine, 1% antibiotic/antimycotic (all from GIBCO), and 50 µM 2-mercaptoethanol (Sigma).

Virus-specific CTLp prevalence was determined by using a modification of a well established limiting dilution assay (Tripp et al., "Cytotoxic T-lymphocyte precursor frequencies in BALB/c mice after acute respiratory syncytial virus (RSV) infection or immunization with a formalin-inactivated RSV vaccine," *J Virol* 72:8971 (1998)). In brief, different dilutions of responder cells in 0.1 ml of TCM were added to wells (24 wells/dilution) of round-bottom, 96-well microtiter plates (Costar) with 0.1 ml of APCs. The APCs were syngeneic splenocytes that had been incubated in a serum-free MEM (GIBCO) containing $10^7$ pfu/ml RSV for 3 h at 37° C. and resuspended at $10^7$ cells/ml in TCM containing 20% EL4.1L-2 supernatant (the lymphoma cell line, EL4.IL-2 (ATCC TIB 181), endogenously secretes IL-2). The responder cells and APCs were incubated at 37° C. for 7 days in a humidified atmosphere. The contents of individual wells were then divided in two and placed into replica plates and incubated for 6 h with $10^4$ $^{51}$Cr-labeled, RSV-infected or mock-infected target cells. The virus-specific CTLp frequency was estimated using linear regression and 95% confidence intervals about the slope of the regression line plotting the number of cells versus the number of nonresponding cultures. A responding well was defined as one in which the mean $^{51}$Cr release from RSV-infected targets plus responding cells was ≧3 SD from the mean of $^{51}$Cr release from control wells containing uninfected target cells plus responding CTLp. The virus-specific CTLp frequency was estimated according to the Poisson equation at the 37% nonresponding culture point ($F_0$) along the slope of the linear regression line. The 95% confidence intervals were used to determine significance, which is indicated by p<0.05%.

Figure 5:
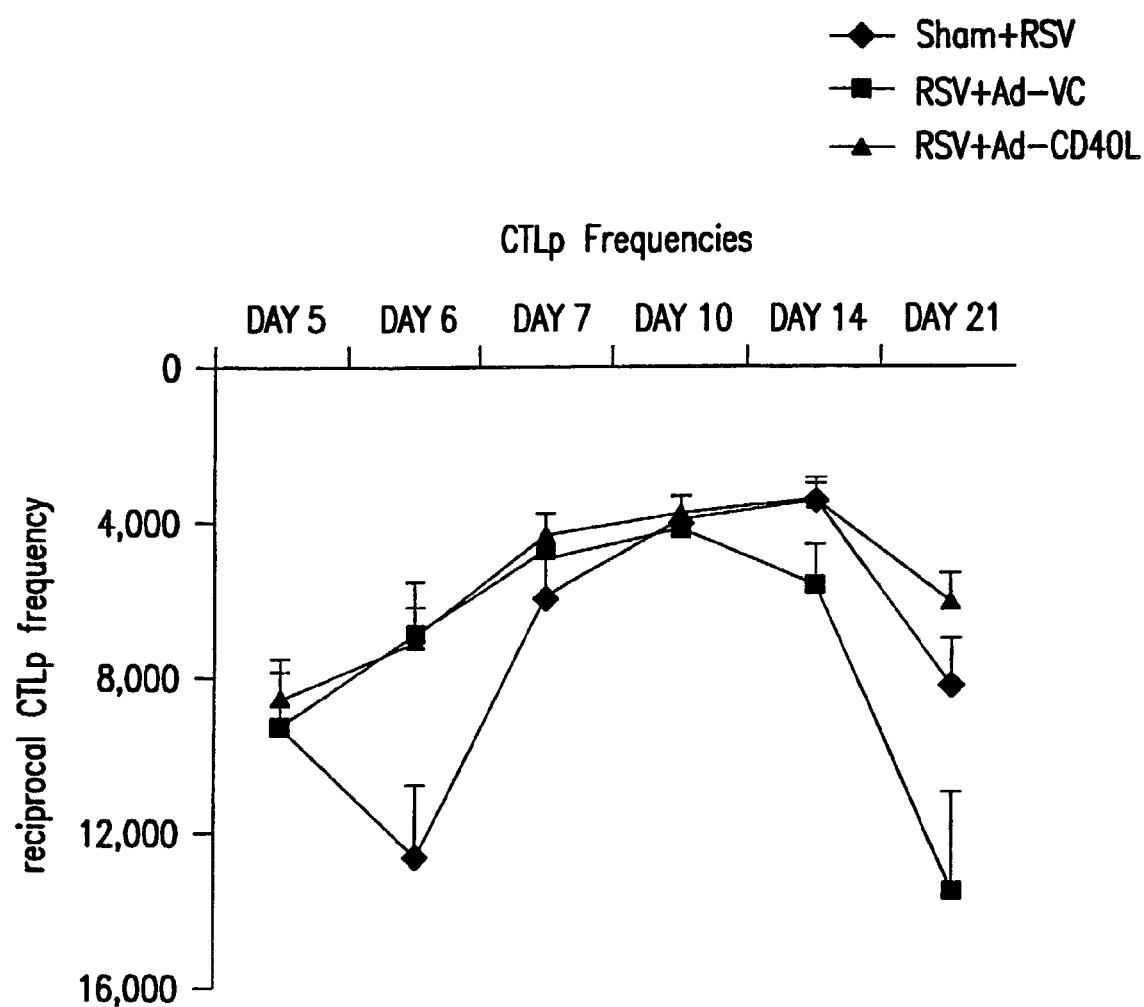
FIG. 5. is a graph of CTLp frequencies during the immune response of mice simultaneously challenged with RSV intranasally and given intraperitoneal injections of saline (sham-treated), or Ad-VC or AD-CD40L. The frequencies of class I-restricted CTLp and the ranges are shown for 9 experiments. Significant differences are given by 95% confidence limits.

To address the effect of coincident CD40L expression on the pulmonary RSV-specific CTLp frequency, MHC class I-restricted CTLp frequencies were measured in the BAL from sham-treated mice, Ad-VC-infected and Ad-CD40L-infected mice at various times following RSV challenge (FIG. 5). The average values from all experiments (n=9) are summarized and show that infection with Ad-CD40L helps to sustain a higher frequency (average 1:6,000) of RSV-specific CTLp at a later time point (day 21 post-infection) in the lung, than either the sham treatment (average 1:8,200) or Ad-VC-infected (average 1:13,500) mice. Peak CTLp frequencies for all treatments following RSV challenge occurred between day 10 and 14 post-infection (range 1:3,300-1:4,100). After day 14 post-infection, there was a greater decrease in RSV-specific CTLp in the lungs of sham-treated and Ad-VC-infected mice, whereas there was less of a decline in CTLp frequency for Ad-CD40L infected mice, especially when compared to the Ad-VC control.

EXAMPLE 5

CD40L Expression Enhances Anti-RSV Antibody Titers

The effect of treatment with recombinant adenoviruses and plasmids expressing CD40L on antibody titers and isotypes was evaluated. Infection of mice with recombinant viruses and collection of cells and organs was carried out as described in Example 1.

For these experiments DNA vaccines were prepared using pcDNA3.1 vector plasmids (Invitrogen Corp., San Diego, Calif.) constructed with G or F gene cDNA from RSV/A2 (Sullender W., "Antigenic analysis of chimeric and truncated G proteins of respiratory syncytial virus," *Virology* 209:70 (1995)) or the murine CD40L cDNA (SEQ ID NO:1)(Dilloo et al., 1997)). G gene DNA vaccine (pcDNA-G), F gene DNA vaccine (pcDNA-F), murine CD40L DNA vaccine (pCD40L) and control (pcDNA3.1 only) plasmid constructs were propagated in *E. coli* SURE2 cells (Stratagene, La Jolla, Calif.) and purified using a EndoFree Plasmid Giga Kit (Qiagen, Valencia, Calif.). For immunization, DNA plasmids were precipitated onto 1-micron gold microcarriers (BioRad, Hercules, Calif.) according to the manufacturer's instructions. Mice were anesthetized with Avertin (2,2,2-tribromoethanol), their abdomen hair shaved and immunized in two different locations in the m. obliquus externus abdominis with 20 µg DNA vaccine/immunization under helium velocity using the Helios Gene Gun (BioRad, Hercules, Calif.). Using a similar immunization procedure, mice were boosted with a total of 40 µg DNA vaccine once a week for 3 weeks. To confirm plasmid expression in vivo, sera from eye bleeds was collected weekly and analyzed by ELISA for antibodies against RSV-infected and uninfected Vero cells.

Antibody titers and isotypes were determined in the following manner: Mice were anesthetized with Avertin and 200 µl of peripheral blood collected from the eye capillary bed. The sera from the peripheral blood was collected and analyzed for RSV antibodies by enzyme-linked immunoabsorbant assay (ELISA) with RSV-infected or uninfected Vero cell lysate-coated microtiter plates and peroxidase-conjugated anti-mouse Ig (Accurate, Westbury, N.Y.). Ig isotypes were determined using an isotyping kit according to the manufacturer's instructions (Pierce, Rockford, Ill.). Specimens were tested at 2-fold dilutions from 1:100 to 1:3200. The ratio of absorbance from RSV-infected over the absorbance of uninfected Vero cell lysate was used in the analysis of ELISA results.

To determine the effect of CD40L expression on the anti-RSV antibody response, mice were sham-treated with PBS, infected with Ad-VC or infected with Ad-CD40L and simultaneously challenged with RSV, the sera collected and analyzed at days 14 and 21 post-infection. As the same rank order of immunoglobulin isotype concentrations (IgG2a>IgG2b>IgG1>IgM>IgG3>IgG1) applied to all groups examined, no distinct Th1- or Th2-type humoral pattern emerged in relation to any of the infections. However, mice infected with Ad-CD40L did develop a higher titer of anti-RSV antibody, (i.e., a 2-fold higher increase in titer at day 21 post-infection (1:3,200) compared to sham-treated mice (1:1,600) or mice infected with Ad-VC (1:1,600)).

To determine if CD40L could augment the antibody response to RSV, mice were intradermally immunized each week for three consecutive weeks with the empty plasmid DNA vector or with the vectors that encoded F or G subunits or F-CD40L, G-CD40L or F-G-CD40L and then challenged one week later with RSV (FIG. 6). Peak antibody titers after DNA immunizations but before RSV challenge ranged between 1: 100-1:200. After RSV challenge, anti-RSV antibody titers exceeded 1:3200 for all mice except those immunized with the G subunit vector alone (FIG. 6). The anti-RSV antibody responses were enhanced by the addition of the CD40L vector as indicated by higher absorbance ratios at the 1:3200 dilution (FIG. 6). A striking 7-fold increase in the antibody response (i.e., absorbance ratio) to the G subunit vector was induced by the addition of CD40L.

EXAMPLE 6

Expression of CD40L During RSV Infection or Immunization Enhances the Overall Immune Response and Promotes a Th1 Over a Th2 Response Expression of CD40L during RSV infection or immunization appear to enhance the overall immune response and promote a Th1 over a Th2 type response.

Our studies revealed that CD40L expression coincident with RSV infection or coexpressed during DNA vaccination had broad immune-enhancing effects. CD40L enhanced the levels of IL-2 and IFNγ (FIGS. 1 and 3), increased pulmonary NO synthesis (FIG. 4), increased the frequency of RSV-specific CTL precursors in the lung (FIG. 5), increased the anti-RSV antibody response (FIG. 6), and decreased the RSV clearance time (Table 1). Not to be limited by theory, the increase in pulmonary NO production associated with CD40L treatment may have contributed to the more rapid clearance of RSV. NO is believed to inhibit an early stage of viral replication and spread (Pope et al., "Resistance to murine hepatitis virus strain 3 is dependent on production of nitric oxide," *Journal of Virology* 72:7084 (1998)), possibly by activating APC (MacMicking et al., "Nitric oxide and macrophage function," *Annual Review of Immunology* 15:323 (1997)) and the associated increased production by APC of TNFα and IFNγ and activation of by-stander T cells (DeKruyff et al., "Antigen-driven but not lipopolysaccharide-driven IL-12 production in macrophages requires triggering of CD40," *Journal of Immunology* 158:359 (1997)). CD40L expressed by T helper cells is a major contributor to T cell dependent NO production by macrophage and reduced macrophage production in CD40L-deficient mice enhanced susceptibility to Leishmania infection (Soong et al., 1996; Stout et al., 1996). The increased expression of TNFα and IFNγ and enhanced antibody response could also contribute to the accelerated clearance of RSV from the lungs (Table 1).

Although an overall increase in RSV-specific CTLp frequency with CD40L expression was not observed, the higher CTLp frequency observed at 21 day post-infection compared to control treatments raises the possibility that CD40L may enhance the duration of the RSV-specific CTL response (FIG. 5). In studies of CD40L$^{-/-}$ mice infected with lymphocytic choriomeningitis virus (LCMV) and Pichinde virus, the primary CTL response was normal, but the memory response was defective (Borrow et al., 1996).

Finally, co-expression of CD40L with F and G proteins enhanced the RSV antibody response with later RSV challenge (FIG. 6). This priming effect was most pronounced for the anti-G antibody response. Since a high titer of neutralizing RSV antibodies may be needed for effective protection as has been shown in passive antibody studies (Hemming et al., 1995; Fixler "Respiratory syncytial virus infection in children with congenital heart disease: a review," *Pediatric Cardiology* 17:163 (1996)), we presume the same may also apply for RSV vaccination. If this is the case, then expression of CD40L with a RSV vaccine may enhance RSV antibody response and thus the protective immune response.

In summary, our results indicate that supplementary expression of CD40L broadly enhances the RSV immune response and directs this response toward a Th1 phenotype. The results suggest that CD40L can enhance RSV immunity and might be a useful adjuvant for a RSV vaccine.

Throughout this application, various patents, publications, books, nucleic acid and amino acid sequences have been cited. The entireties of each of these patents, publications, books, and amino acid sequences are hereby incorporated by reference into this application.

What is claimed is:

1. A method for enhancing an immune response to respiratory syncytial virus (RSV), said method comprising administering to a mammal an effective amount of an RSV vaccine comprising a vector comprising a nucleic acid sequence encoding an RSV F protein or an RSV G protein and an effective amount of a source of a CD40 binding protein.

2. The method of claim 1, wherein the CD40 binding protein is selected from the group consisting of a CD40 ligand, a CD40 ligand fusion protein a monoclonal antibody that specifically bind CD40, and combinations thereof.

3. The method of claim 2, wherein the CD40 binding protein is CD40 ligand.

4. The method of claim 3, wherein the source is a vector comprising a promoter operatively linked to nucleic acids encoding the CD40 ligand.

5. The method of claim 4, wherein the vector is a plasmid.

6. The method of claim 4, wherein the vector is an adenovirus vector, an avipox vector or a canarypox vector.

7. The method of claim 4, wherein the mammal is a human.

8. The method of claim 7, wherein the mammal is a human whose genome comprises a wild type CD40 ligand gene.

9. The method of claim 1, wherein the immune response comprises a TH 1 cytokine immune response.

10. The method of claim 1, wherein the immune response comprises an antibody response.

* * * * *